(12) United States Patent
Carr

(10) Patent No.: US 7,351,540 B1
(45) Date of Patent: Apr. 1, 2008

(54) PROTEIN ISOLATION AND ANALYSIS

(75) Inventor: Francis J. Carr, Aberdeen (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/937,100

(22) PCT Filed: Mar. 17, 2000

(86) PCT No.: PCT/GB00/01015

§ 371 (c)(1),
(2), (4) Date: Sep. 20, 2001

(87) PCT Pub. No.: WO00/57183

PCT Pub. Date: Sep. 28, 2000

(51) Int. Cl.
*G01N 33/53* (2006.01)
*C12Q 1/68* (2006.01)

(52) U.S. Cl. .............. 435/7.1; 435/6; 435/5; 435/4; 435/DIG. 15; 435/DIG. 14; 435/DIG. 3; 435/DIG. 2; 530/387.1

(58) Field of Classification Search .......... 435/7.1, 435/6, 4, 5, DIG. 15, DIG. 14
See application file for complete search history.

(56) References Cited

U.S. PATENT DOCUMENTS

| | | | | |
|---|---|---|---|---|
| 5,849,877 | A | * | 12/1998 | Ring ................. 530/387.1 |
| 5,866,344 | A | * | 2/1999 | Georgiou ............... 435/7.21 |
| 6,300,064 | B1 | * | 10/2001 | Knappik et al. ............ 435/6 |
| 6,734,022 | B2 | * | 5/2004 | Hutchens et al. ......... 436/173 |
| 2002/0192687 | A1 | * | 12/2002 | Mirkin et al. ............. 435/6 |

FOREIGN PATENT DOCUMENTS

| WO | WO 92 15679 A | | 9/1992 |
|---|---|---|---|
| WO | WO 95 16209 A | | 6/1995 |
| WO | WO98/59360 | * | 12/1998 |

OTHER PUBLICATIONS

Chen et al, The Journal of Biological Chemistry, 270 (40), Oct. 1995, 23398-23401.*
Matthews et al, Scinec, 260, 1993, 1113-1117.*
J M Kerr et al. : "Encoded Combinatorial Peptide Libraries Containing Non-Natural Amino Acids" Journal of the American Society, US, American Chemical Society, Washington, DC, vol. 115, No. 115, Mar. 24, 1993 XP002128603.
Nikolaiev V et al.: "peptide Research Peptide-Encoding For Structure Determination Of Nonsequenceable Polymers Within Libraries Synthesized And Tested On Solid-Phase Supports" Peptide Research, US, Naticok, MA vol. 6, No. 3, 1993, pp. 161-170, XP00867524.
Cao P. et al.: "Analysis of Peptides, Proteins, Protein Digests, and Whole Human Blood by Capillary Electrophoresis/Electrospray Ionization-Mass Spectrometry Using an In-capillary Electrode Sheathless Interface" Journal of the American Society For Mass Spectrometry, US, Elsevier Science Inc. vol. 9, No. 10, Oct. 1, 1998, pp. 1081-1088, XP004140548.
Von Leoprechting Achim; Hoerth Patric; Haehnel Wolfgang; Schilz Emile; Muehlenhoff Ulrich: "Identification of biotinylation sites on proteins by selective retrieval of 2-iminobiotinylated peptides from proteolytic peptide mixtures: Localization of the accessible lysine residues on the photosystem I subunits PsaD and PsaE" Analytical Biochemistry, vol. 262, Sep. 10, 1998,pp. 110-121, XP002143247.
Ducret Axel; Van Oostveen Inge; Eng Jimmy K; Yates John R III, Aebersold Ruedi: "High throughout protein characterization by automated reverse-phase chromatography/electrospray tandem mass spectrometry" Protein Science, vol. 7, Mar. 1998, pp. 706-719, XP000922504.
Wang Baiyang; Chen Yi-Ben; Ayalon Oran; Bender Jeffrey; Garen Alan: "Human single-chain Fv immunoconjugates targeted to a melanoma-associated chondroitin sulfate proteoglycan mediate specific lysis of human melanoma cells by natural killer cells and complement" Proceedings of the National Academy of Sciences of the United States of America, vol. 96, Feb. 16, 1999, pp. 1627-1632, XP002143248.
Geng M et al.: Signature-peptide approach to detecting proteins in complex mixtures: Journal of Chromatography, NL, Elsevier Science Publishers B. V. Amsterdam, vol. 870, No. 1-2, Feb. 18. 2000, pp. 295-313, XP004187331.
P L Courchesne et al.: Identification of Proteins by Matrix-Assisted Laser Desorption/Ionization Mass Spectroscopy Using Peptide and Fragment Ion Masses (from 2-D Proteome Analysis Protocols, Ed. A. J. Link) Methods in Molecular Biology, US, Humana Press Inc., No. 112, 1999, pp. 487-511, XP002103063.

* cited by examiner

*Primary Examiner*—T. D. Wessendorf
(74) *Attorney, Agent, or Firm*—Millen, White, Zelano, Branigan, P.C.

(57) ABSTRACT

Novel methods for the identification and/or sequencing of proteins are provided. These methods are particularly suited to screening antibody libraries and in preferred embodiments make use of mass spectrometry techniques for direct or indirect sequencing.

3 Claims, No Drawings

PROTEIN ISOLATION AND ANALYSIS

The present invention relates to the isolation and analysis of proteins especially by mass analysis. The invention has particular application to the isolation of binding proteins such as antibodies. The invention also provides for modification of proteins or protein fragments in order to facilitate mass analysis and/or the isolation of specific proteins encode by members of a gene library.

For the isolation of proteins, the invention provides new methods for isolating specific proteins from a complex mixture of such proteins by virtue of binding to a specific target. In particular, the invention provides methods for isolating specific antibody domains from a gene library-derived mixture of such domains by virtue of binding to a specific target antigen. For the analysis of proteins, the invention provides new methods for analysing complex mixtures of proteins especially to compare proteins between two or more different samples.

For the isolation of proteins from complex mixtures by virtue of binding to a specific target and where the identity or amino acid sequence of the protein is unknown beforehand, it has usually been very difficult to isolate enough protein which binds to the target for direct characterisation of the protein. In order to select a protein of interest from a large library of natural, synthetic or semi-synthetic proteins, "protein display" methods have been developed whereby recombinant proteins are produced physically linked to their genes such that recovery of the proteins allows subsequent rapid recovery of the genes. Such methods include "in-vivo" display methods such as display on bacteriophage ("phage display"), bacteria and yeast, and include "in-vitro" display methods such as display on ribosomes ("ribosome display"). The recovered genes can be sequenced in order to determine the identity of the recovered protein or can be used to regenerate the recovered protein. If a library of genes is subject to protein display methods whereby proteins are selected for a particular characteristics such as binding to an antigen (for antibody variable regions), then at each selection round, the recovered genes will be enriched for those encoding proteins exhibiting such particular characteristics. Disadvantages of current "in-vivo" display methods include a limit to the amount of functional protein displayed (phage display is usually limited to polypeptides of less than 40 kDa), the usual need to fuse the recombinant protein to a host protein (which may interfere with the function or binding of the recombinant protein), and an inability to vary the number of proteins displayed per display particle; the latter is also a problem with "in-vitro" display methods such as ribosome display. In addition, methods for the selection of proteins with particular characteristics such as binding to an antigen are limited due to the small sizes of the display particles such that methods such as fluorescence activated cell sorting (FACS) cannot readily be used. Thus, there remains a need for new methods to improve the isolation of proteins from complex mixtures, in particular to improve the isolation of antibody variable regions (Fv's) from complex mixtures of Fv's. This, the present invention provides for improved methods for isolation of proteins from complex mixtures. In particular, the present invention combines the use of protein libraires generated from gene libraries with improvements in mass spectrometry and especially improvements in matrix-assisted laser desorption/ionisation time-of-flight (MALDI-ToF) spectrometry and the ability to directly sequence ToF-separated peptides by tandem mass spectrometry (MS-MS) and, more recently, the ability to combine ToF and MS/MS into one device (Q-ToF) and the ability to combine HPLC and electron spray (ES), tandem mass spectrometry. The present invention also includes new methods for screening for individual proteins from complex protein mixtures whereby these proteins are not "displayed" i.e. bound to their corresponding genes either during or after binding to the target. The present invention also includes new methods for screening for individual proteins from complex protein mixtures whereby neither the proteins nor the target are "displayed" i.e. bound to any other molecule or structure. The present invention also includes new methods for screening for individual proteins from complex protein mixtures whereby the proteins and their corresponding genes are linked together via the addition or inclusion of an "associating moiety" whereby the proteins bind to the target either before or after addition of the "associating moiety".

Thus, in a first aspect, the present invention provides a method of protein identification, screening and/or sequencing comprising providing a library of individual proteins, one or more of which may bind to a target of interest, wherein each individual protein includes in its sequence a "barcode" sequence, which can be used to identify each individual protein in the library.

This aspect of the present invention provides for libraries of proteins, especially recombinant antibody domains such as Fv's, whereby individual protein members of the library include, within their amino acid sequence, a tract of sequence (a "barcode") which can subsequently be sequenced in order to identify which protein(s) has bound to the specific target (or, in the case of Fv's, "antigen"). This embodiment will apply especially where the Fv's are derived from human genes whereby the selected Fv may be suitable for human therapeutic or diagnostic use. In this particular application, an extensive gene library of Fv's is created from a pool of immunoglobulin cDNA's such as those derived from peripheral blood B cells in humans or such as pools created synthetically using human variable regions with semi-randomised ("combinatorial") CDRs (complimentarity-determining regions) at one or more positions. If this gene library is created in such manner that a random (or semi-random) gene sequence is included within the Fv coding region or terminal to this region, then such a random/semi-random gene sequence will generate a random/semi-random peptide sequence associated with individual Fv's. Such a random/semi-random gene sequence is created using standard methods such as oligonucleotide priming/DNA polymerase extension or PCR whereby a random/semi-random synthetic oligonucleotide sequence is used as one of a pair of primers used to amplify immunoglobulin gene fragments during the creation of the Fv gene library. If members of the Fv library comprise two chains (i.e. heavy and light chain-derived chains (VH and VL)) as opposed to a single-chain (VH and VL joined by a peptide linker), then individual barcodes can be associated with each of the chains (or can be associated with one of the chains only). Upon creation of the library, the resultant Fv's each include one or more "peptide barcodes" unique to that particular Fv or to a small subset of Fv's from within the complex library. Preferably, the peptide barcode is C terminal to the single-chain Fv region or C terminal to the VH or VL or both and includes, flanked between itself and the Fv region, one or more protease sensitive sites such as sites for enterokinase (cleaves after Asp-Asp-Asp-Asp-Lys (SEQ ID NO: 1), Factor Xa (cleaves after IIe-Glu/Asp-Gly-Arg) or other endopeptidases. If a mixture of such Fv's is produced from a suitable gene library, then this mixture is mixed with a target antigen (or antigens such as on cells), usually where the antigen is immobilised. This results in specific Fv's binding to the target antigen with non-binders (or weak binders depending on the stringency of washing) being washed away. Having washed away excess antibodies, the remaining antigen/Fv complex is then usually released from the Fv by digestion with the endoprotease used to cleave the introduced protease sensitive site. This released barcoded peptide is then subjected to mass analysis/mass spectrometry sequencing either directly or, if desired, following capture by virtue of specific amino acids or amino acid sequences which allow the peptide to be captured onto a solid phase such a cysteine residues which can be biotinylated for subsequent capture on immobilised avidin or streptavidin. Alternatively, any other method can be employed to determine the sequence of the peptide barcode either within the Fv or after release including using specific ligands which bind to the barcode in a sequence-specific manner. Having determined the sequences (or part-sequence) of barcodes derived from bound Fv's, corresponding synthetic oligonucleotides are then produced and used to specifically amplify or enrich for specific Fv genes from the library. These specific or enriched Fv (or VH and VL) genes are then further used to generate corresponding Fv's which could then be retested for antigen binding either individually or as part of a small pool of isolated Fv's. Ultimately, by this method, specific Fv's can be generated with desirable antigen binding properties and, if from a human source, potential clinical utility. This aspect also encompasses the use of multiple barcodes associated with individual proteins or Fv's, for example two adjacent barcodes at the C terminus of Fv's whereby two peptides are released from each Fv by protease digestion, either simultaneously in order to enhance the identity of Fv's which bind to the target, or sequentially whereby different proteases are used in successive rounds of digestion to provide a different means to subsequently amplify Fv genes corresponding to Fv's which bind to the target. This aspect also encompasses the use of multiple barcodes which are analysed at the same time in order to increase the diversity of overall barcode sequences to provide specific coding of individual proteins. This aspect also encompasses the use of barcodes within individual proteins, for example within one or more CDR positions of an Fv. This aspect also encompasses the use of proteases which might also digest the protein components of the protein: target mixture or, additionally, any protein agent used to immobilise the target, with the proviso that the barcode peptides released from the bound test protein(s) can still be detected and sequenced within the background of other peptides. In the preferred format of this aspect, a single region of barcode is provided at the C terminus of the light chains forming a soluble Fab fragment whereby VHs and VLs are encoded by the same expression cassette or cistron such that the barcode sequence can be used to access both VH and VL genes. Such an Fab fragment can be conveniently produced using a range of expression systems, for example the M13 bacteriophage vector system where, by introduction of secretory leader sequences, the heavy and light chains of Fabs are secreted into the periplasmic space of the host bacteria and harvested from that space. The vector system is first prepared with in-frame barcodes by cloning in mixtures of synthetic oligonucleotides. For the formation of two adjacent barcodes, this is conveniently undertaken by sequential cloning or oligonucleotide mutagenesis whereby pooled M13 recombinants containing the first mixed barcode are prepared as a template for subsequent cloning of the second in-frame barcode. Preferably, the barcoding is designed such that the encoded protein contains endonuclease sites both flanking and between the two barcodes and also whereby a "spacer" region adjacent to one of the barcodes creates a peptide including that barcode which has a higher molecular weight than the other barcode. By judicious design of barcodes and the use of multiple barcodes in this manner, there is provided an option to simply analyse masses of endoprotease-released peptides by, for example, MALDI-ToF whereby the sequences of the peptides can be deduced (or near deduced) such that synthetic oligonucleotides can be designed to isolate (or enrich) for the specific proteins with the barcode(s) detected by MALDI-ToF analysis. Such deduction of these sequences is achieved by design of sequences whereby specific amino acids only occur in one or two positions along the peptide. For example, where the peptide is designed using 17 of the 20 natural amino acids (hereby designated A-Q), then the sequences might be designed with options for any of three amino acids at each position along the peptide sequence as follows;

| aa position: | 1 | 2 | 3 | 4 | 5 | 6 | 7 | 8 |
|---|---|---|---|---|---|---|---|---|
| amino acid options: | A | C | E | G | I | K | M | O |
| | B | D | F | H | J | L | N | P |
| | C | E | G | I | K | M | O | Q |

This design would give a theoretical 6561 different peptide sequence barcodes. If an adjacent barcode with a spacer region is also designed on the same basis, then this would give an additional 6561 different barcodes. In combination, this would create $4 \times 10^7$ barcode sequences which would be adequate to uniquely tag most members of a protein library of such size. The use of additional adjacent barcodes or longer barcodes based, for example, on use of two specific amino acids at any position in the sequence (thus creating 262,144 different barcode sequences using 19 amino acids) would increase the diversity of barcodes provided. In practice, codon redundancy is reduced through the judicious choice of codons at each position in the sequence during design of mixed synthetic oligonucleotides. One design of oligonucleotide for an 8 amino acid barcode peptide for MS/MS sequencing is as follows;

```
Codons-
NAC NCC NGG NTG TKC VAG GNV CNT (SEQ ID NO:2)
Amino acids-
 N   T   R   L   F   Q   D   H  (SEQ ID NO:3)
 D   P   G   M   C   E   V   L
 H   A   W   V       K   A   P
 Y   S                   G   R
                         E
where codons N = A, C, G or T
K = G or T
V = A, C or G
4 x 4 x 3 x 3 x 2 x 3 x 4 x 4 = 13824 barcode
sequences
```

Specific codons can also be incorporated by discontinuous oligonucleotide synthesis whereby specific codons are added sequentially to separated mixtures of previously synthesised oligonucleotides ("codon mutagenesis"). Once a candidate barcode sequence is deduced by MALDI-ToF or MS/MS and where the diversity of individual barcodes is less than that of the library, the corresponding specific oligonucleotide (or mixture of oligonucleotides if there is redundancy in codon usage) can be used as a PCR primer in conjunction with an opposite primer designed from the protein or vector system to enrich for genes encoding the protein from which the barcode was detected. Where adjacent barcodes are used, a second primer nested within a gene fragment created from the first primer can then be used to enrich for the gene encoding the actual protein detected. If required, the above method can incorporate three or more barcodes in order to increase the specificity of oligonucleotide-directed enrichment of specific genes encoding the desired protein. It will be understood by those skilled in the art that this first aspect of the invention can cover a number of variant methods with the underlying principle that a specific protein is recovered from a library of such proteins via mass or sequence analysis of one or more peptides associated with or encoded by that specific protein and, as such, that this aspect has a broad utility in isolating genes encoding desired proteins where only peptide sequence is determined or deduced.

It will be understood by those skilled in the art that, within the scope of the present invention, there are many variations of the first aspect. For example, it will be understood that peptide barcodes could be incorporated into pairs or groups of proteins which are then allowed to bind in order to determine which proteins binds to each other by virtue of detecting barcodes from each of the proteins engaged in binding. As an alternative to isolation of proteins from complex mixtures, proteins within these complex mixtures which demonstrate certain binding properties such as binding to other macromoles such as DNA can be detected using the present method. The present method includes a variety of ways for adding peptide barcodes to proteins including methods where the barcode is encoded within the gene fragment encoding the protein. However, barcodes can be added to such proteins or to any other suitable mixture of molecules by direct attachment of peptides. For example, specific peptides can be added to specific antibodies or proteins using a range of chemical or photochemical methods. One application of such a method is to label one complex mixture of proteins with one barcode (or selection of barcodes, for example with different protein specificities) and the other barcode to an alternative complex mixture of proteins, for example to differentially barcode proteins from two different samples which are then mixed. It will be understood by those skilled in the art that the principle of adding peptide barcodes to proteins or other molecules could also be applied to non-peptide barcodes whereby such barcodes can be directly identified (or nearly identified) using mass or sequencing methods. As such, the barcodes could include nucleic acid barcodes attached to proteins or other molecules including nucleic acids. As with peptide barcodes, such nucleic acid barcodes can be analysed by mass spectrometry to provide an accurate estimate of mass. Such barcodes might be released from the proteins or other molecules using restriction enzymes instead of proteases.

It will be understood by those skilled in the art that, within the scope of the present invention, there are applications of the first aspect other than in the isolation of proteins. For example, the distribution of proteins or other ligands within a live organism can be analysed by analysis of barcodes by mass or by sequence which are associated with specific organs within the organism. In the analysis of peptide or protein binding specificity to other molecules, barcodes can be constructed as part of the peptide or protein binding regions in order to analyse specificity by mass or sequence analysis of barcodes. For example, mixed peptide barcode sequences can be constructed around known anchor residues of MHC molecules and the spectrum of peptides which bind to specific MHC molecules then determined by elution and mass or sequence analysis of the barcode.

In a second aspect, the present invention provides A method of screening a protein library comprising screening said library for one or more desired properties, followed by dereplication to identify one or more individual proteins in the library having the desired property.

This aspect of the present invention provides for libraries of proteins, especially recombinant antibodies such as Fv's, whereby individual members of the libraries are isolated for binding to specific targets whereby pools of proteins from the library are screened individually and then positive pools are subjected to one or more rounds of dereplication until the individual proteins in the library which bind to the target are identified. Specifically, this aspect relates to screening protein libraries without use of a display system i.e. where there is either no physical association of the proteins with corresponding genes. In this aspect, pools of proteins are screened for binding to the target whereby either the target is labelled to indicate which pool(s) contain proteins which bind, or where the target is detected without labelling. A particularly favoured method is to screen pools of proteins in solution without any fusion or attachment to other moieties (which might influence the binding of proteins to their targets) and then to precipitate the total protein pool (together with any attached target) prior to mass analysis, especially via MALDI-ToF, in order to screen for a "fingerprint" of ionised peaks which is representative of the target and therefore indicates if the target has bound. Once one or more positively-binding pools are identified, these can be then dereplicated either to reduce the complexity of the pool or to segregate out individual proteins for screening for binders to the target. In practice, a particularly favourable way of assembling pools of proteins is to firstly to assemble pools of genes encoding these proteins. If genes are cloned into plasmid or phage vectors for example, these can be pooled by mixing together individual bacterial colonies or plaques, or more conveniently by segregating pools of colonies/plaques by plating onto separate agar plates (at densities such as 1000 colonies/plaques per plate) and scraping/eluting colonies/plaques from these plates into one mixture which is then used for synthesis of the proteins either through bacterial/phage expression or through in vitro transcription/translation. In a similar manner, other microorganisms or in vitro synthesis systems could be used for synthesis of proteins. This aspect also encompasses the use of complex targets such as mixtures of molecules, whole cells or cell membranes whereby the molecular target yields a mass analysis "fingerprint" which is characteristic for binding to a specific molecular target within the complex target. This aspect also encompasses, where the target is a protein, the use of proteases to digest the target(s) in order to produce a peptide mass fingerprint indicative of the target and which, where the protease also digests the protein(s) from the library, can still be detected even within a background of other peptides derived from the library. This aspect also encompasses a range of different types of "target" and criteria for selection of pools of proteins or individual proteins other than by binding to a target. For example, the aspect encompasses the use of biological assay systems as a criteria for selection of proteins, for example where proteins are selected for the ability to stimulate or inhibit a biological activity. Other formats of binding assays would include inhibition of binding of a ligand to its receptor and selection for proteins which bind to certain locations on a target where the target might be, for example, a molecule, cell or tissue section.

In a third aspect, the present invention provides A method of protein identification and/or sequencing comprising providing a library of individual proteins, one or more of which may bind to a target of interest, wherein each individual protein, together with its gene, is bound to an "associating moiety".

This aspect of the present invention provides for libraries of proteins, especially recombinant antibodies such as Fv's, whereby the proteins and their corresponding genes are linked together via the addition or inclusion of an "associating moiety" whereby the proteins or Fv's bind to the target either before or after addition of the "associating moiety". The associating moiety serves the purpose of enabling regeneration of the proteins or Fv's via the associated corresponding gene, for example by PCR amplification (or other means of amplification such as via bacterial transformation, or by direct sequencing and subsequent regeneration via this sequence). Where the proteins or Fv's are generated as a pool with a corresponding pool of genes, then genes associated with the proteins or Fv's which bind to the target (or which do not bind if so desired) are used as the basis for regeneration of individual or smaller pools of proteins or Fv's in order to repeat screening to identify the specific proteins or Fv's (via the corresponding genes) which bind to the target.

A particular format for this third aspect where the associating moiety is a particle and whereby recombinant proteins and their corresponding genes are co-immobilised on particles whereby recovery of an individual particle provides for identification of the gene or genes encoding the recombinant protein. This format particularly relates to methods whereby genes encoding the recombinant proteins are co-immobilised on the same particle as their corresponding proteins such that upon selection for the recombinant protein, the corresponding gene will also be selected such that the identity of the selected protein can be determined (by sequencing the gene) or such that further recombinant protein can be generated from the gene. The method of the invention include provisions to control the amount of proteins displayed on the particle commonly by controlling the number of moieties on the particle to which the recombinant proteins bind. The invention includes provisions to co-display other molecules on the particle in conjunction with the recombinant protein including other proteins or protein chains and including molecules to which the recombinant proteins bind such as antigens.

In the basic operation of the third aspect of the present invention, there is provided an array of genes or mixtures of genes from which are synthesised recombinant proteins using methods such as in vitro transcription and translation or phage display, such proteins being exemplified by antibody variable regions (Fv's). Subsequently, genes and recombinant proteins are co-immobilised on particles, one or more ligands are associated with the gene either as DNA or mRNA whereby such ligands become bound to a "receptor" on the particle surface or whereby such ligands are reacted with the particle surface to produce a covalent or ionic attachment. Alternatively, the gene is directly immobilised on the particle via formation of one or more covalent or ionic bonds to natural DNA or RNA reactive groups. The resultant recombinant proteins encoded by the genes may have one or more ligands associated (such ligands being moieties on the proteins by which immobilisation can be achieved) such as protein sequence tags (encoded by the genes) or biotin groups (incorporated by in vitro transcription and translation using biotinyl lysine) such that they too can become bound to a "receptor" on the particle surface or whereby such ligands are reacted with the particle surface to produce a covalent or ionic attachment. The ligands on the genes and proteins can either be the same or different ligands with immobilisation on the same or different receptors. For useful operation of this aspect of the invention, genes or pools of genes either as DNA, mRNA or within a live microorganism such as a phage, are distributed into arrays (or multiple reaction vessels etc) and recombinant proteins are produced in such arrays (for example by in vitro transcription and translation or by growth of phage). Master arrays containing the genes can be used as the source of material for generating the recombinant proteins whereby samples of genes or proteins are dispensed into server arrays such that array locations for each gene or protein pool is preserved. Either before, during or after this process, one or more particles is introduced into each position in the array providing receptors to which genes and proteins can bind. On one variation of the invention, the genes are attached to the particles at the outset and proteins produced directly from these genes such that these recombinant proteins are subsequently immobilised onto the same particle. Either before or following attachment of recombinant proteins to the particles, the proteins can be optionally subjected to modification for example phosphorylation by other kinases or binding by other proteins. In a variation of the third aspect, the arrays include droplets such as oil-in-emulsion droplets or liposomes into which genes or live microorganisms are segregated (usually by producing the droplets prior to protein synthesis and thus arraying the genes within droplets). Proteins are produced within the droplets and these are then co-attached to the particles including the genes. In the case of droplets, the particle to which the genes and proteins co-attach can either be introduced into the droplet or the particle can be the droplet itself. For example, in the case of liposomes, the proteins could be produced with lipophilic tags which combine with the liposomes membranes especially where this leads to "display" of the proteins on the outside surface of the liposome. A related example is where in vitro translation of mRNA is used where microsomal membranes can be introduced in to the reaction whereby proteins with lipophilic tags can integrate into such membranes which can subsequently be dispersed into small particles.

If it is desirable to then pool the particles for a selection process, particles are then retrieved from the arrays and mixed; the recombinant proteins on the particles are then subjected to selection, typically by exposure to a target which binds to selected proteins on the particles. Certain recombinant proteins could also be subjected to modification at this stage. Particles holding selected or modified proteins could then be retrieved by a variety of methods; for example, if the target is labelled with a fluorescent label, FACS could be used to separate out particles with (or without) the target. In the first major aspect of the present invention, genes encoding recombinant proteins on such selected particles could then be recovered by, for example, PCR amplification of the co-immobilised DNA or mRNA.

There are many types of "associating moieties" for linking proteins with their corresponding genes which could be used in the third aspect of the present invention. Particles of use include latex and magnetic particles, and particles onto which synthetic oligonucleotides are synthesised directly. Such particles would commonly be provided with a "receptor" to which the synthesised polypeptides can bind. Other associating moieties may be single molecules or molecular complexes which can act as a bridge to join the gene molecules to the synthesised proteins. For example, both the gene molecules and synthesised proteins can include biotin groups which could then be cross-linked by addition of streptavidin whereby streptavidin acts as the associating moiety. In a similar fashion, a sequence tag on the proteins and a ligand on the gene molecules can be cross-linked using, for example, a bispecific binding reagent such as a bispecific antibody (binding to both sequence tag and ligand) or an antibody-streptavidin conjugate (whereby the antibody binds either to a ligand on the protein or gene and the streptavidin binds to biotin on the protein or gene, whichever is non-liganded). Other associating moieties may be bacteria or bacteriophage whereby the synthesised polypeptide binds to a specific ligand on the bacteria or bacteriophage. For example, an M13 expression system can be used to produce a Fv fragment of a specific antibody in E. coli which can then bind to a specific protein antigen on the M13 itself, especially where this is displayed on the phage head fused to a capsid protein. By testing for M13 phage to which Fv has bound, the gene encoding the specific Fv can be determined by sequencing the Fv gene encoded by the M13. Similarly, the M13 expression system can be used to produce a protein which binds to a specific protein displayed on the M13 itself. In every case, the unique feature of the third aspect is that the recombinant protein molecules become attached, after synthesis, to the corresponding genes via an associating moiety. Such attachment after synthesis especially allows for the unhindered synthesis of the protein molecules without, for example, the need to be synthesised as a fusion with other protein molecules which could alter the protein conformation or interfere with its recognition or function.

The present invention includes several methods to generate the recombinant proteins prior to linkage to the associating moiety. These methods especially include protein synthesis by in vitro transcription and translation, and protein synthesis in bacteria directed by plasmids or phage. In the latter case, the present invention provides the advantage that the generated protein need not be fused with a phage protein as the generated protein in the present invention is subsequently immobilised onto a separate particle. In contrast to current methods for phage display of proteins where such proteins are fused to a surface phage protein or protein which can reach the surface, the third aspect of the present invention would require either lysis of the phage or for secretion or leakage of the recombinant protein from the phage head in order to provide for its subsequent immobilisation onto the particle. Other in vivo methods of generating proteins such as expression in bacteria, yeast or even mammalian cells could thus also be used in the third aspect which therefore has the advantage of being more versatile than individual display methods. Thus, recombinant proteins could be modified by a particular host, for example glycosylated by mammalian cells, prior to immobilisation. One particularly useful aspect of the present invention is the ability to control the numbers of molecules of recombinant protein on the associating moiety, especially when this is a particle, by control of the number of "receptor" molecules on the particle. In the case of antibody variable regions therefore, the valency of individual or pools of antibodies can be varied according to selection criteria. A further alternative associating moiety could be a live cell itself whereby the recombinant protein is linked to a ligand on or near the surface of the live cell such as a cell surface marker of the bacterium or mammalian cell harbouring the expression plasmid or whereby, upon secretion, the protein would then bind to the cell from which it was expressed. The protein could then be reacted with target and cells harbouring the expression cassette for the specific Fv binding the target could be isolated.

The third aspect herein provides a particularly useful means for selection of recombinant proteins which bind to a target or for selection of recombinant proteins which are modified by a specific treatment, for example by treatment with cell or tissue lysates. The method accordingly will prove especially useful for the molecular evolution of recombinant proteins whereby successive rounds of selection ensure recovery only of proteins with stringent properties such as high affinity binding to a target. The method can also encompass successive rounds of mutagenesis of selected genes to maximise the diversity for evolutionary selection. It will be apparent to those skilled in the art that there are many variations which could be employed based on the third aspect of the present invention but falling within the scope of the present invention. For example, associating moieties especially particles used to capture the genes and recombinant proteins could themselves be bound by another polypeptide chain whereby, when protein-protein binding occurs, the recombinant protein is not captured by the particle directly but rather by the polypeptide chain already on the particle. An appropriate tag or ligand on the recombinant protein can then be used to provide a means for detecting the protein-protein binding event. In the same manner, particles could be bound by synthetic oligonucleotides which are subsequently used to anneal to the genes as a means to capture them on the particles.

In a fourth aspect, the present invention provides A method of protein identification and/or sequencing comprising providing a library of individual proteins, one or more of which may bind to a target of interest, wherein each individual protein is attached to an individual "coding moiety".

In this aspect of the present invention, recombinant proteins synthesised from a gene library are subsequently attached to "coding moieties" such as particles which are distinguishable through one or other coding methods in such a manner that the coding relates to the identity of the gene which encodes a recombinant protein attached to the particle. Where the recombinant proteins are immobilised on coded particles, the recombinant proteins may have one or more ligands associated such as protein sequence tags or biotin groups such that they can become bound to a "receptor" on the coded particle surface or whereby such ligands are reacted with the particle surface to produce a covalent or ionic attachment. In the operation of this aspect of the present invention, recombinant proteins or pools of proteins are synthesised or segregated in large arrays. Particles with unique codes are then introduced into each position in the array. Such codes include, for example, different ratios of measurable signalling moieties such as fluorescent, chemiluminescent or radioactive labels or different physical features which distinguish particles such as different shapes or markings, for example a code or unique mark etched into the particle. In each case, individual coded particles can be distinguished from each other. Particles of use in the present invention includes any such particles, complexes or molecules with the property that proteins can be attached. Following pooling of particles and binding of the mixtures of proteins on coded particles to a specific target, the coding of selected particles could then be determined in order to determine their original array positions and hence the array loci of genes encoding the selected recombinant proteins. As a variation of these aspects of the invention, selected proteins on particles could be identified directly using methods such as MALDI-TOF (mass spectroscopy) or using labelled antibodies to identify known proteins. The operation and scope of this fourth aspect of the present invention will share many aspects and scope of the above third aspect of the invention.

35. In a fifth aspect, the present invention provides A method for analysing mixtures of proteins comprising:
   (i) digestion or cleavage of the protein mixture;
   (ii) fractionation of the resultant peptides; and
analysis of the resultant peptides by means of their mass and/or sequence.

This aspect of present invention relates to methods for analysing mixtures of proteins. In particular, the invention relates to methods to compare proteins between different cells and tissues. The invention involves the combination of digestion or cleavage of protein mixtures, fractionation of peptides using a library of protein binding reagents, and subsequent analysis of peptide fractions for mass or sequence. The invention includes optional physical fractionation of proteins or peptide fragments additional to fractionation with protein binding reagents. Current methods to analyse en masse complex mixtures of proteins such as in mammalian cells or tissues require that the proteins are separated by technologies such as two dimensional (2D) gel electrophoresis. For this technology, cellular proteins are usually separated on the basis of charge in one dimension and on the basis of size in the other dimension. Proteins can either be identified with reference to the electrophoresis migration pattern of a known protein or by elution of the protein from the electrophoretically separated spot and analysis by methods such as mass spectrometry and nuclear magnetic resonance. However, limitations of the 2D protein gel method include the limited resolution and detection of proteins from a cell (typically only 5000 cellular proteins are clearly detected), the limitation to identification of separated proteins (for example, mass spectrometry usually requires 100 fmoles or more of protein for identification), the specialist nature of the technique and the difficulty in automating the technique in order to achieve very high protein analysis throughputs. There is thus a need for superior methods to analyse complex mixtures of proteins en masse especially using methods without gel electrophoresis and methods which are easy to automate.

The core of the fifth aspect is that proteins are either digested or cleaved into smaller peptide fragments and then fractionated using a library of protein affinity reagents and then subjected to mass analysis especially by mass spectroscopy. Optionally, proteins or peptide fragments may be fractionated physically in addition to being fractionated with protein affinity reagents and may also be conjugated with one or more "chemical tags" to assist in fractionation.

The major aspect of the fifth aspect provides for cleavage of proteins using proteases or chemical methods; fractionation of the peptide mixture thereby produced and subsequent mass analysis. Fractionation of peptides is achieved using protein affinity reagents, especially libraries of recombinant antibody fragments. Optionally, the method includes additional fractionation of proteins or peptides using physical methods or specific affinity reagents such as antibodies or solid phases or reactive chemical groups to isolate peptides or mixtures of peptides for subsequent mass analysis. Protein affinity reagents are used to retrieve individual peptides or sets of peptides from the peptide mixture for subsequent mass analysis. Alternatively or additionally, protein affinity reagents can be used to eliminate peptides from the mixture whereby the mixture is itself subsequently subjected to mass analysis. The protein affinity reagents can either bind by virtue of specific sequences or structures in peptides or by virtue of specific chemical groups either as natural constituents of the peptides or as chemical tags which are added to the peptides either before or after cleavage.

For analysis of larger mixtures of peptides, panels of protein affinity reagents such as those provided by recombinant libraries of antibody Fv fragments (including single-chain Fv's) can be used in order to isolate subsets of peptides for subsequent analysis. Such panels of Fv's will include a wide range of peptide specificities which could be achieved, for example, by pre-absorbing antibody libraries on the peptide samples of interest or by immunising animals with peptide samples of interest and generating recombinant Fv libraries from the animal B cells. Alternatively, polyclonal antisera or panels of monoclonal antibodies could be prepared from immunised animals and used to fractionate peptides. Then individual or mixtures of the selected antibodies are used to isolate (or eliminate) the specific subsets of peptides from a test sample. Subsequent mass analysis of a range of peptides can facilitate the detection of differences in specific proteins between test samples.

Generation of recombinant Fv's or antibodies to all peptides in a mixture is difficult and is highly dependant on the number of peptides in a mixture and the facility for individual peptides to be bound with reasonable affinity to antibodies ("antigenicity"). With a very large peptide mixture, a limitation is redundancy whereby antibodies with the same peptide specificities are repeatedly represented whilst antibodies to other peptide specificities are underrepresented or absent. This may cause a particular protein not to be mass analysed if none of the peptides from a particular protein are bound by an antibody. Therefore, a particularly useful method is to isolate N or C terminal peptides (or both) from a protein by preabsorption of the protein to a solid phase via its N and/or C terminus prior to cleavage or by chemical tagging of the N and/or C terminus for subsequent isolation after cleavage. In principle, this then should lead to recovery of all N and/or C terminus peptides representing all proteins from the sample. Such isolation of N and/or C terminal peptides is greatly facilitated by the differential reactive nature of the N terminal amino group and the C terminal carboxyl group in the protein compared to internal amino and carboxyl groups. Such isolated N and/or C terminal peptides can be further fractionated using other affinity reagents which either recognise specific peptide sequences or which recognise chemical tags on the peptides or further fractionated by physical means such as HPLC. Such isolated N and/or C terminal peptides are then fractionated using protein affinity reagents prior to mass analysis. The invention also allows for sequential conjugation of different chemical tags to the protein/peptide mixture especially where N or C termini are sequentially exposed by specific cleavage of the protein/peptide and whereby the N or C termini (or both) are conjugated with a specific chemical tag upon exposure of that termini. This aspect of the invention therefore provides for a series of protein fractions with a range of conjugated chemical tags introduced at the termini, such fractions being isolated using an affinity reagent which binds to the tag. As a particularly useful method as an alternative to a chemical tag at the terminus of the protein molecule, chemical tags can also specifically be attached to non-terminus amino acids such that internal peptides can be isolated via an internal chemical tag. Unique chemistries are available for attachment of ligands to several specific amino acids, for example to the $\epsilon$-amino groups of lysines, the thiol groups of cysteines and the carboxyl groups of aspartic and glutamic acids. One advantage of isolating peptides by virtue of non-terminal tags is that selection can be made for larger peptides which are more likely to contain a specific amino acid to which a tag is attached thus isolating peptides with a mass which exceeds low molecular weight masses with a larger background noise during mass analysis. Another advantage is the array of reagents already available to introduce chemical tags onto specific amino acids within proteins or peptides especially reagents which provide a biotin tag.

Another embodiment of the fifth aspect provides for sequential cycles of protein cleavage using proteases or chemical methods with fractionation with protein affinity reagents either during or following successive protein cleavage steps and subsequent mass analysis. In this case, the analysis of protein mixtures is assisted by sequential cleavage cycles whereby the spectrum of proteins and peptides are fractionated with the protein affinity reagents and analysed following each cleavage cycle. This method could also include chemical tagging cycles between cleavage cycles to increase the mass or steps to remove side-groups such as carbohydrate groups in order to reduce mass. If the mass of the range of protein fragments is then determined at the end of each cleavage cycle (either with or without chemical tagging, cleavage or other modification), then a range of mass distributions will be obtained for each cycle. With an appropriate series of mass modification cycles, the result for a single protein or a mixture will be a mass spectrum of protein/peptide fragments which is altered at successive cycles; the pattern of these alterations will provide a "fingerprint" for the specific proteins/peptides in the mixture. The appearance and disappearance of a particular protein/peptide fragment of a certain mass following a specific cleavage cycles with or without chemical tagging, cleavage or other modifications will provide a fingerprint for identification of the fragment sequence especially by reference to a database of such fingerprints. Comparison of the spectrum of protein/peptide fragments from different related samples then allows for the identification of protein/peptide fragment differences between these samples. Particularly useful in this aspect of the present invention is proteases which specifically recognise two amino acids and cleave the protein as a result. An example of such proteases are the prohormone convertases which cleave between dibasic amino acid pairs. Therefore, the fifth aspect of the present invention provides for novel ways of analysing protein mixtures using a combination of protein digestion or cleavage, fractionation using protein affinity reagents and mass analysis.

In a related aspect of the fifth aspect, proteins are fractionated prior to cleavage. For large protein mixtures, particularly those isolated directly from whole cells or tissues, the pre-fractionation of proteins may be desirable in order to reduce the complexity of mixtures subjected to subsequent cleavage, peptide fractionation and mass analysis. Whilst protein affinity reagents which bind sequences or structures in the proteins/peptides directly are primarily useful, an alternative or an addition is to use a library of chemical tags to provide moieties bound by a set of protein affinity reagents. More conventional means of pre-fractionation include the use of gel electrophoresis either in one or two dimensions where sections of the gel are isolated and the proteins within then subjected to cleavage and mass analysis. Other pre-fractionation methods include isolation of proteins by virtue of natural modifications such as phosphorylation, glycosylation, protein-protein (or peptide) interaction; alternatively, membrane proteins can be pre-fractionated or proteins from particular compartments within the cell. Another important pre-fractionation procedure is to remove highly abundant proteins from the mixture using affinity reagents such as antibodies to bind and remove such proteins. As an alternative to pre-fractionation, peptides generated after cleavage can also be fractionated by many of these means and also including size/charge fractionation methods using HPLC. Such methods are particularly useful to fractionate peptides which have already been selected from a mixture through the application of protein affinity reagents. In particular, HPLC can be interfaced with mass analysis such that peptide fractions from HPLC separation are directly subjected to mass analysis. Peptides generated after cleavage can also be fractionated by virtue of natural modifications using, for example, antibodies which bind phosphorylated amino acids within peptides. Prefractionation of proteins may also be achieved by using protein affinity reagents such as monoclonal/polyclonal antibodies to isolate specific proteins for subsequent cleavage and mass analysis. For such analysis of larger mixtures of proteins, libraries of antibodies such as those provided by recombinant libraries of Fv's are preferred in order to isolate subsets of proteins or subsets of cleaved peptides for subsequent mass analysis. Such library of antibodies will include a wide range of protein or peptide specificities but can also be pre-enriched for binding to proteins/peptides of interest in the particular sample of interest. For peptides, this is preferably achieved by testing individual Fv's for selective binding to a single or a small number of peptides in the sample. Alternatively, pre-enrichment can be achieved by pre-absorbing antibody libraries on the mixed protein/peptide sample of interest and then using individual or mixtures of the selected antibodies in order to isolate subsets of proteins or peptides. Fractionation with protein affinity regents provides mass spectra for a range of different protein/peptide fractions thus facilitating detection of differences in specific proteins between samples.

A further advantage of the use of chemical tags is that the subsequent fractionation of peptides by affinity reagents can greatly reduce the number of selected peptides from a protein molecule with the rest of the molecule thus being eliminated from the mass analysis. An especially convenient method for selective chemical tagging is to tag either (or both of) the N and C terminus of the protein molecules in the mixture and then to digest or cleave the protein molecules with a reasonably selective reagent such as a amino acid or sequence-specific protease (such as endopeptidase Arg-C) or cleavage reagent (such as acid pH to cleave at Asp-Pro). Using an affinity reagent, N or C terminal peptides (or both) from the original protein could then be isolated and all internal peptides discarded. This reduction in complexity is then sufficient for mass analysis especially using HPLC coupled to a tandem mass spectrometer to analyse the peptides en masse in order to identify the individual peptides from the mixture. Alternatively, chemical tagging could be performed only after digestion/cleavage, for example with the dibasic cutters, the prohormone convertases. This would provide for tagging only at one or more internal sites of the original proteins. If the protein mixture is then subjected to a second digestion/cleavage step with a different enzyme or cleaving reagent, then the size of the tagged peptides would be reduced where a cleavage site was present in the original protein. The tagged peptides could then be fractionated using protein affinity reagents and subjected to mass analysis.

In another embodiment of the fifth aspec, a protein mixture is subjected to cycles of tagging, digestion/cleavage and mass analysis, whereby fractionation by protein affinity reagents and mass analysis is performed only on an aliquot of the mixture resultant from use of an affinity reagent binding to the specific chemical tag and whereby the master mixture is then subjected to tagging with a different chemical tag and digestion/cleavage. This provides sequentially a range of different fragments. Another variation on the method involves the same initial steps as above but, having exposed new N and C termini after cleavage, one (or both) of these new termini can then optionally be tagged with a different chemical which thus tags internal sites in the original protein. If required, the process could be repeated one or more times with a different protease or cleavage reagent, each time with the addition to the N or C terminus of a different chemical tag. In one format of the method, the whole mixture of proteins would first be tagged with two different chemical groups at each of the N and C terminus and then cleaved with a protease, such as one which specifically cuts adjacent to a specific amino acid, and tagged again at the new N and C termini with two further different chemical groups. This would result in a mixture of peptides each with chemical tags at the termini. As the N and C terminal peptides would have a specific tag, these could then be isolated from the mixture using appropriate affinity reagents. Internal peptides without either the initial N or C terminal tags could be isolated using their specific tags. The process of digestion and tagging could then be repeated to create further peptides with tags. Using specific combinations of affinity reagents for specific tags, N or C terminal or specific internal peptides from the original protein could then be isolated and selected peptides discarded to achieve a reduction in complexity. Where chemical tags are added to two or more amino acid side groups within peptides, sequential use of affinity tags could isolate fractions of peptides containing specific combinations of amino acids. For example, if a mixture of peptides of average length of 20 amino acids and separately tagged at lysine and phenylalanine and the mixture comprises 25% of peptides which include neither lysine or phenylalanine, 25% with lysine only, 2.5% with phenylalanine and 25% with both, then the separate or sequential use of specific affinity reagents either for lysine or phenylalanine will result in fractionation of peptides into four equal fractions. In practice, such a fractionation scheme will favour the binding of larger peptides to affinity reagents as these peptides are more likely to contain one or more of the specific amino acids tagged. This will bias against the very small peptides such as those with molecular weights less than 1000 daltons which, when subjected to mass spectrometry analysis, will be more likely to coincide with background noise due to fragmented peptides and other small molecules.

Where analysis of complex protein mixtures is required such as in mammalian cells or tissues, the present invention provides a main method where proteins are fractionated using protein affinity reagents either before or after cleavage and the peptides are then mass analysed. The fractionation of a complex mixture of proteins or peptides requires a correspondingly complex mixture of protein affinity reagents and can be assisted by one or more additional affinity reagents which can recognise features of the proteins/peptides which are the basis for fractionation. Where cleavage is conducted prior to fractionation, the most common method used in the present invention is to cleave the whole protein mixture with a protease such as trypsin or V8 (Glu-C) protease and to then selectively isolate and mass analyse certain peptides.

Commonly, N or C terminal peptides (or both) from the peptide mixture are isolated typically by adding a chemical tag to the N and/or C terminus of the proteins prior to cleavage and using an affinity reagent which isolates peptides with the chemical tag. Alternatively, specific peptides (N/C terminal or otherwise) can be isolated using affinity reagents which have been selected for binding to specific peptides within specific proteins; these will then select out those peptides from the mixture. For more complex mixtures of proteins, a further fractionation step such as HPLC fractionation based on size, charge or hydrophobicity is preferred prior to mass analysis especially as this can be interfaced with mass analysis. Selective isolation of peptides then allows for comparative analysis of specific peptides derived from alternative protein mixtures for their relative quantities (relating to relative levels of the proteins in their respective mixtures) and, in certain cases, for modifications of the peptides.

For fractionation of N or C terminal peptides, the preparation and use of protein affinity reagents is an important aspect of the present invention and the labelling of the N or C terminus of proteins is another important aspect. With a typical mixture of proteins from mammalian cells or tissues or from many living organisms, several of the N termini of these proteins (and some C termini) will be modified (for example, by methylation) such that addition of a chemical tag to the terminus may be blocked. In addition, a typical mixture of proteins from mammalian cells or tissues or from many living organisms, the proteins will occur at different relative levels of abundance including, commonly, certainly highly abundant proteins. Where protein mixtures from mammalian cells or tissues or from other living organisms are used for the initial selection of protein affinity reagents, such highly abundant proteins may dominate selection of affinity reagents and may be predominant in the final peptide mixture for mass analysis. A solution to both of these problems is to use an artificial source of mixed proteins to isolate the affinity reagents. Typically, this will be a gene expression system whereby a gene (usually cDNA) library is used to generate the proteins without N or C terminal modifications. In addition, the use of a gene expression system allows the gene library to be "nornalised" to reduce or remove highly abundant genes within the library. This is typically achieved by self-annealing of the DNA (or RNA) prior to constructing the library. Therefore, a common method in the present invention is to generate proteins by expression of gene libraries (usually normalised) resulting in proteins free from significant N or C terminal modifications and, where normalised, resulting in a protein mixture free from domination by specific proteins. A typical expression system used with gene libraries is in vitro transcription and translation using a eukaryotic ribosome preparation; this also provides the possibility of incorporating modified amino acids into the expressed proteins. The expressed protein mixture can then be used directly for N or C terminal labelling. Other expression systems could also be used where N terminal amino groups or C terminal carboxyl groups are not modified or prevented from subsequent chemical tagging. Where modification occurs, in some cases the N terminal modification can be removed either using enzymes such as histone deacetylase or chemical methods such as limited cyanogen bromide cleavage to remove N terminal methionines.

Having produced a mixture of proteins free from N/C terminal modification, chemical tags can then be added to the N/C terminal amino group(s). For the N terminus, the $\epsilon$-amino group of lysines can be initially blocked using reagents such as citraconic anhydride or methyl acetimidate to then allow only the N terminal amino groups to react. Alternatively, the $\epsilon$-amino group of lysines can be blocked by incorporating modified lysines into the expression system such as in vitro transcription/translation whereby, for example, biotin-modified lysines can be directly incorporated instead of lysines. Chemical tags can then be added selectively to the N terminus of proteins, for example using isothiocyanates of specific molecules to which an affinity reagent is available. One such example is fluorescein which is incorporated by reaction of the proteins with fluorescein isothiocyanate allowing subsequent purification with anti-fluorescein antibodies. Alternatively, polycarboxylic chelating agents can be incorporated as isothiocyantes allowing subsequent purification with specific metals. Once the N and/or C termini of proteins in the mixture are tagged, the protein is then comprehensively and specifically cleaved either chemically or enzymatically, using proteases such as trypsin or another cleaving agent. Such cleavage thereby releases from each protein an individual tagged terminal peptide fragment, such collection of fragments which can then be purified from the mixture of untagged peptides using an appropriate affinity reagent such as an antibody specific for the chemical tag. If required, the size of the chemical tag can be increased in order to produce a larger mass for analysis; this would be useful for peptide fragments resulting from cleavage very close to the chemical tag whereby the resultant fragment might be so small as to be mass analysed within lower molecular weight "noise". The chemical tag night, for example, comprise a piece of nucleic acid attached to the peptide via a reactive group introduced during synthesis of the nucleic acid. Such a nucleic acid molecule might also be useful for isolation of the tagged peptide via annealing of the nucleic acid to a complimentary sequence.

Following chemical tagging and isolation, the recovered mixture of N/C terminal peptides are then used as a "bait" for the isolation of protein affinity reagents to bind to these same peptides from proteins derived directly from mammalian cells or tissues or from other living organisms. Such affinity reagents will typically derive from a library of recombinant Fv's displayed as part of a particle containing the corresponding gene encoding the antibody. Examples of such particles are ribosome display particles or phage display particles, in each case where the genes from selected antibodies can be rescued in order to propagate those specific antibodies. As an alternative, large arrays of antibodies (such as recombinant single chain or Fabs, Fvs) can be screened using the N/C terminal peptide mixture and antibodies which display binding to the peptides can be recovered via the corresponding genes. As another alternative, N and/or C terminal peptides could be used to directly generate polyclonal or monoclonal antibodies by appropriate immunisation of an animal. By these means, a library of protein affinity reagents is selected which can then be used for the analysis of mixtures of proteins such as from mammalian cells or tissues or from other living organisms. Such analysis can either involve using the library of affinity reagents to select out N/C terminal peptides from proteins derived from mammalian cells or tissues or from other living organisms or using individual affinity reagents to select out individual peptides. The selected peptides can then be mass analysed typically by MALDI-ToF (matrix-assisted laser desorption/ionisation time-of-flight) where the individual peptides give individual charge:mass ratios which can then be used to identify the peptide amino acid constituents. MS-MS (double mass spectroscopy) peptide sequencing can subsequently be used to identify the peptide if it can be isolated. Alternatively, the new generation of Quadrupole-ToF LC-MS-MS ("Q-ToF") instruments can provide for sequential MALDI-ToF and MS-MS within the same instrument. Indeed, protein affinity reagents either individually or in mixtures can be immobilised either indirectly or directly onto the desorption chip inserted into the MALDI-ToF instrument and peptides can be subsequently bound via the affinity reagents on the chip. In this way, multiple peptide fractions adsorbed by multiple affinity reagents at different loci can be analysed on a single chip. The use of recombinant proteins as the "bait" to isolate protein affinity reagents also provides the prospect of attaching other tags to those proteins whereby the tags are encoded by the gene sequence; for example, a C terminal polyhistidine tag (allowing subsequent purification of the tagged fragments using nickel chelates) could be incorporated, for example through PCR-mediated incorporation into the gene sequences.

The use of recombinant proteins as the "bait" to isolate protein affinity reagents also provides another common method of the fifth aspect of the present invention for specifically isolating peptides using tags encoded by the recombinant proteins. Such tags can be conveniently incorporated into members of the a gene (usually cDNA) library during its construction or into individual clones or groups of clones thereof using specific PCR primers encoding such tags and designed to incorporate such tags into the resultant expressed proteins. Preferably, such tags will be incorporated into the expressed proteins in all reading frames in order to produce a productively tagged protein. Such tags will preferably be incorporated via the downstream primer of a PCR reaction with the usual result that the tag is produced towards the C terminal end of the expressed protein (although upstream termination codons may prevent this in some clones). However, tags may also be incorporated at the N terminal end or in both N and C termini.

For the isolation of specific peptides from a peptide mixture, the peptide sequences can be produced synthetically (or via recombinant DNA) and then, as above, used as the "bait" to capture specific protein affinity reagents. These affinity reagents can then be used to isolate these same peptides from a cleaved protein mixture derived from, for example, mammalian cells or tissues or from other living organisms.

As an alternative to selectively fractionating N or C terminal peptides or specific internal peptides, modified peptides such as peptides including phosphorylated amino acids which can be isolated using antibodies which selectively bind to phosphorylated amino acids (tyrosine, threonine or serine or combinations thereof) or using immobilised $Fe^{3+}$ to trap negatively charged peptides. Similarly, peptides modified by glycosylation and other modifications can be isolated, in some cases where the peptide modification is further derivatised in order to facilitate isolation. For example, carbohydrates can readily be modified via periodate reactions as an intermediate to adding chemical tags such as fluorescein. A particularly important aspect of the invention is the fractionation of selectively modified peptides whereby such peptides are selectively tagged by virtue of their differential exposure to tagging within the original protein environment prior to cleavage. For example, surface exposed proteins on living cells can be selectively tagged, for example with biotin, by treating the cells with a tagging agent which preferentially reacts with specific amino acid groups. An indirect method for achieving such tagging in proteins which are naturally tagged via other stimuli within cells is to apply such stimuli in order to effect tagging of the proteins. For example, receptor-associated tyrosine kinase molecules within cells can potentially be tagged (for example, phosphorylated) by addition of the receptor ligand to those cells. Following modification, peptides are released from proteins by cleavage and then directly mass analysed or subjected to fractionation with protein affinity reagents as above prior to mass analysis.

Mass analysis of proteins and peptides by the present invention is preferably performed using mass spectroscopy. In particular, MALDI-ToF analysis has the capability to very accurately measure specific mass: charge ratios for individual peptides. This method has the capability for simultaneous analysis if thousands of peptides. Above 4 kD, the resolutiion of individual peptides (and proteins) becomes poorer such that cleavage of proteins into peptide fragments is necessary in order to provide fine resolution. Recent methods of interfacing liquid chromatography separation methods (such as HPLC) with tandem mass spectroscopy has already permitted the mass spectrum analysis of protein mixtures comprising up to 200 proteins. As such proteins are analysed following protease digestion, if an average ten peptides per protein is assumed, then the method can analyse up to 2000 peptides. Using methods of the present invention whereby, for example, only tagged N terminal peptides are analysed, then up to 2000 N terminal peptides derived from up to 2000 proteins could be analysed at any one time. As this is not sensitive enough for an en masse analysis of mammaliari proteins from cells (typically 50,000 per cell), then peptides have to be segregated into at least 25 fractions in order for these fractions all to be analysed. Such further fractionation can be achieved either directly using a pre-selected library of protein affinity reagents, or by the use of reagents to label internal ends after successive protein digestion/cleavage steps following which specific protein affinity reagents are used to fractionate peptides according to their tags. As an alternative to standard mass spectroscopy, MALDI-TOF can be used to produce protein mass profiles which can be compared for protein mixtures from different cells.

Chemical tags are typically moieties which can be covalently attached to proteins usually at the N or C terminus. For chemical tagging of the N terminus, this is commonly undertaken at the terminal amine group. If it is necessary to avoid tagging of the $\epsilon$-amino group of lysines, then these can be initially blocked using reagents such as citraconic anhydride or methyl acetimidate. Terminal amine groups are then reactive with a wide range of chemical reagents especially using isothiocyanates. Thereby, common antibody-recognised ligands such as dinitrophenol and fluorescein can then attach these to the N terminus for subsequent fractionation using an antibody affinity reagent. For example, the commonly used Edman reagent phenyl isothiocyanate can be used to specifically attach to the N terminus of proteins and can be derivatised if necessary with a moiety provided for subsequent binding to an affinity reagent. For chemical tagging of the C terminus, methods based on carbodiimide activation are commonly used to introduce ligands which are bound by affinity reagents. Alternatively, addition of moieties to the C terminus of proteins has been described using reverse proteolysis whereby certain proteases such as carboxypeptidase Y and lysyl endopeptidase can work in reverse to add chemical tags, commonly by way of amino acids either as derivatised amino acids with tags for binding to an affinity reagent or by way of natural sequences of amino acids which can then be specifically bound by an affinity reagent. It will be recognised that a wide range of internal amino acids can also be chemically tagged including Lys via the $\epsilon$-amino group, Glu/Asp via the carboxyl group, Cys via the thiol group, Ser/Thr via the hydroxyl group and Tyr via the hydroxyphenyl group. Specific derivatisations of most other amino acids have been described. It will also be recognised that post-translation protein modifications can be used for addition of chemical tags especially with glycosylation where the sugar residues are commonly oxidised by periodate to formaldehyde groups which can then react with amine-containing molecules. Other modifications which can be used to add chemical tags include lipidation, phosphorylation and metal ion addition. It will be recognised that there are a large number of methods in the art for introducing one or more chemical tags at specific sites within protein molecules or peptides.

Protein affinity reagents for use in the fifth aspect are commonly monoclonal antibodies. For specific sequences or structures within proteins or peptides, a library of recombinant antibody binding sites usually in the form of Fab's, Fvs or single-chain Fv's is used where commonly the antibody binding sites are "displayed" using, for example, bacteriophage or ribosome complexes such that the gene encoding individual antibody binding sites can be recovered. For use in the present invention, libraries of antibody binding sites can be dispersed into groups, for example by picking and arraying phage plaques or picking and arraying genes in vectors for ribosome display. Such pools will usually contain antibody binding sites for several proteins or peptides such that the pools can be used for fractionation. Alternatively, the protein or peptide mixture to which libraries of antibody affinity reagents are required can be immobilised and used as the target for the pre-selection of suitable affinity reagents which are then dispersed into pools or used as individual reagents. For chemical tags, individual monoclonal antibodies are used to specifically bind to individual tags in order to achieve subsequent fractionation.

The fifth aspect of the present invention includes the use of protein affinity reagents other than monoclonal antibodies where such reagents can facilitate the fractionation of peptides or proteins prior to mass analysis. Such affinity reagents would include molecules of the immune which selectively bind certain peptides such as major histocompatability proteins and T cell receptors. Other protein affinity reagents would include protein domains commonly involved in protein-protein binding interactions such as SH1 domains. Included in the present invention is the concept of cyclising peptides including within mixtures and especially when bound to solid phases by, for example, linking cysteine residues under reducing conditions. One method for this would be to add an additional cysteine residue at an exposed N or C terminal on immobilised peptides using, for example for C terminal immobilised peptides, standard conditions of peptide synthesis or using reverse proteolysis whereby certain proteases such as carboxypeptidase Y and lysyl endopeptidase. Included in the fifth aspect is also a method for further fractionating proteins or peptides by adding, usually at the N terminus, amino acids which form part of the recognition sequence of a protease which specifically cleaves at a recognition sequence of two or amino acids whereby one or more terminal amino acids in the protease recognition site is provided by the starting protein or peptide. In this manner, only a fraction of the proteins or peptides to which the new amino acids are added will be then subject to terminal protease cleavage by virtue of the newly created sequence. In this manner, proteins or peptides can be tagged with additional amino acids usually at the N terminus creating, in a fraction of the thus tagged mixture, a specific protease cleavage site. The proteins or peptides can then, for example, be immobilised via the new terminus for example using a tagged terminal amino acid or by adding a chemical tag to the terminus, whereby an affinity reagent is then used to immobilise the tagged moieties. After removing non-immobilised untagged molecules, the proteins or peptides can then be subjected to cleavage with the specific protease which will then only cleave where the cleavage site has been generated by a combination of synthesis-derived amino acids and the original protein or peptide-derived amino acids. The cleaved peptides can then be fractionated using protein affinity reagents and mass analysed (or further processed prior to mass analysis) thus representing a subset of the peptide mixture. By using parallel synthesis of specific amino acids to exposed termini followed by immobilisation and cleavage, large mixtures of proteins or peptides can be fractionated on the basis of their terminal amino acid(s). An example of a protease recognition site is ile, glu, gly, arg (SEQ ID NO: 4) which is cleaved between gly and arg by Factor Xa. The sequence ile, glu, gly could be synthesised onto the N terminus of a protein or peptide and thus if the adjacent amino acid in the protein or peptide sequence were arg, the cleavage site would be created and could be cleaved by Factor Xa. Other examples of protease cleavage sites are asp, asp, asp, asp, lys (SEQ ID NO: 1), cleaved by Enterokinase between asp and lys; pro, gly, ala, ala, his, tyr (SEQ ID NO: 5) cleaved between his and tyr by genease I; leu, val, pro, arg, gly, ser (SEQ ID NO: 6) cleaved between arg and gly by thrombin. N terminal addition of partial sequence asp, asp, asp, asp (SEQ ID NO: 7) could be used to identify proteins or peptides with N terminal lys (cleaved by enterokinase), pro, gly, ala, ala, his (SEQ ID NO: 8) to identify proteins/peptides with N terminal tyr (cleaved by genease), leu, val, pro, arg (SEQ ID NO: 9) to identify N terminal gly, ser; or leu, val, pro, arg, gly (SEQ ID NO: 10) to identify N terminal ser (cleaved by thrombin). Other proteases such as the MMP's (matrix metalloproteinases) with specific recognition sites could be used to fractionate proteins with other N terminal amino acids. Different protease recognition sites could thus be used in combination with the proteases to fractionate proteins or peptides according to the N terminal amino acid. As an alternative, one or more amino acids are added to the free N terminus of a peptide could be used to create a site for binding by an affinity reagent including where such a site is dependant on one or more the N terminal amino acids from the peptide. Thus, different peptide or groups of peptides could be distinguished by the addition of amino acids to the N terminus which creates, in a manner dependant on the N terminal amino acids, a site for protease digestion or a site for binding by an affinity reagent. Where proteins are used as the starting material especially from mammalian cells whereby the N terminal protein is methionine, this can be removed if required by, for example, formylation and cleavage by a bacterial protease specific for removal of terminal formylmethionine.

Protein affinity reagents are an important aspect of the fifth aspect of the present invention and can be used for both broad fractionation of groups of proteins/peptides or for specific fractionation of individual proteins/peptides. For fractionation, it is first necessary to prepare fractions of or individual protein affinity reagents which binds to a specific fraction or specific peptide and not to other fractions/peptides. A convenient method is to fractionate the proteins or peptides prior to isolation of the protein affinity reagents. In the case of antibodies as the protein affinity reagents, such proteins/peptides can then be used either to bind displayed antibodies from a library or can be used to immunise animals for generation of antisera. Where a library of recombinant antibody binding sites such as single-chain Fv's is used, gene clones encoding these can be retrieved after binding to protein/peptide fractions providing a replicable source of the affinity reagents for subsequent isolation of the specific protein/peptide fraction. Individual single-chain Fv's may, in parallel, be screened for binding specificity, for example by analysing peptide binding by MALDI-ToF. In this case, single-chain Fv's which bind to a single peptide from a large protein mixture are retained (in practice, those binding up to three peptides are also retained) as gene clones for subsequent individual use or use within a mixture of Fv's for isolation of a protein/peptide fraction from the mixture. It will be appreciated that free N termini from proteins are often good targets for isolation of very specific antibodies and therefore capture and release of N terminal peptides from a protein will particularly favour subsequent antibody isolation. Certain Fv's may be useful for the elimination of abundant proteins or peptides from the mixture. It will be appreciated that retention and characterisation of the binding of single-chain Fv's may also provide a means to reduce redundancy by eliminating Fv's with the same specificity as other Fv's.

The various embodiments of the fifth aspect of the present invention cover combinations of protein digestion/cleavage, fractionation with protein affinity reagents and mass analysis with an optional step of fractionation using affinity tags for specific sequences or structures in the proteins or peptides, and an optional step of chemical tagging with fractionation by virtue of these tags. The different aspects encompass different sequences of these steps as follows;

1—repeated digestion/cleavage cycles and mass analysis

2—digestion/cleavage, fractionation with protein affinity reagents, mass analysis 3—fractionation with protein affinity reagents, digestion/cleavage, mass analysis 4—terminal chemical tagging, digestion/cleavage, fractionation with affinity reagents, mass analysis 5—as 3 but with additional cycle(s) of tagging, digestion/cleavage, fractionation 6—as 4 but with repeated tagging, digestion/cleavage cycles and mass analysis The fifth aspect of the present invention should be considered to encompass these and related protein/peptide processing steps with the core objective of reducing the complexity of protein mixtures in order to achieve mass analysis of the resultant protein/peptide fractions.

The currently common method for operation of the invention involves tagging the N and/or C terminus of a mixture of proteins (either natural or encoded by cDNA libraries), cleaving with a protease, immobilising the N and/or C terminal peptide fragments, and releasing and subjecting the peptides to mass analysis. Alternatively, the N or C termini may be modified by addition of amino acids prior to cleavage with a sequence-specific protease. Prior to mass analysis, the peptides are used to bind protein affinity reagents such as antibodies whereby these antibodies have been pre-selected to fractionate the peptides or are themselves retained as affinity reagents. The mixture of proteins may be pre-fractionated, for example by size, or may be produced from cDNA libraries which are pre-fractionated by segregation of clones. The retained protein affinity reagents are then used to analyse complex samples of proteins whereby the antibodies are used to bind peptides which are then mass analysed.

It will be appreciated that many of the same principles described herein for the digestion/cleavage, fractionation and mass analysis of proteins can also be applied to other polymeric molecules such as DNA or RNA. In the case of DNA or RNA, free phosphate and hydroxyl groups at the 5' and 3' termini respectively provide a means for very specific addition of chemical tags or direct binding to a solid phase. Sequence specific restriction or modification enzymes provide for cleavage or modification of DNA molecules. Useful affinity reagents for DNA or RNA are nucleic acids themselves which can be specifically hybridised to a complimentary DNA or RNA sequence with attachment to a solid phase either before of after hybridisation. Using such methods, complex mixtures of nucleic acids can be fractionated and then subjected to mass analysis especially using mass spectrometry.

The invention is illustrated by the following examples which some not be considering as limiting in scope;

EXAMPLE 1

The experiments described in the present example were conducted using a pair of modified single chain antibody (scAbs) genes. Two modified scAbs were prepared consisting of N-terminal epitope tags, the heavy chain variable region (VH), a 14 amino acid linker (EGKSSGSGSESKVD) (SEQ ID NO: 11), the light chain variable region (VL) each fused to the b-zip domain from either the c-jun or c-fos genes.

These constructs were cloned into the vector pET 5c (Rosenberg A H et al., Gene, 56: 125-135, 1987) which provides a T7 promoter followed by the ribosome binding site from T7 gene 10. The scAb constructs were inserted into the vector at an NdeI site such that the sequence encoding the epitope tag followed the first ATG of T7 gene 10. The first construct consisted of a scAb against *Pseudomonas aeruginosa* (Molloy P. et al. *Journal of Applied Bacteriology,* 78: 359-365, 1995) with the FLAG epitope (MDYKD-DDK) (SEQ ID NO: 12) (Knappik A and Pluckthun A, *BioTechniques,* 17: 754-761, 1994) added at the N terminus, and the b-zip domain of c-fos (Abate, C. et al *Proc. Natl. Acad. Sci.* USA. 87: 1032-1036, 1990) at the C-terminal region of the protein. The second consisted a scAb constructed from the anti-foetal antigen antibody 340 (Durrant L G et al. *Prenatal Diagnosis,* 14: 131-140, 1994) with a poly-Histidine tag at the N terminus, and the b-zip domain of c-jun (Abate C. et al, ibid) at the C-terminal region of the protein.

The anti-*Pseudomonas aeruginosa* (α-Ps-fos) scAb and the 340-jun scAb were constructed as described below:

DNA for the α-Ps scAb in the vector pPMIHis (Molloy P et al., ibid) was amplified with the primers RD 5'FLAG: 5'gcggatcccatatggactacaaagac-gatgacgacaaacaggtgcagctgcag3' (SEQ ID NO: 13) (Genosys Biotechnologies Europe Ltd, Cambridge, UK) and RD 3': 5'gcgaattcgtggtggtggtggtggtgtgactctcc3' (SEQ ID NO: 14) (Genosys) which introduced the 5'FLAG epitope sequence and removed the 3' stop codon respectively. The reaction mixture included 0.1 μg template DNA, 2.6 units of Expand Tm High Fidelity PCR enzyme mix (Boehringer Mannheim, Lewes, UK.), Expand HF buffer (Boehringer Mannheim), 1.5 mM MgCl₂, 200 μM M deoxynucleotide triphosphates (dNTPs) (Life Technologies, Paisley, UK) and 25 pmoles of each primer. Cycles were 96° C. 5 minutes, followed by [95° C. 1 minute, 50° C. 1 minute, 72° C. 1 minute] times 5, [95° C. 45 seconds, 50° C. 1 minute, 72° C. 1 minute 30 seconds] times 8, [95° C. 45 seconds, 50° C. 1 minute, 72° C. 2 minutes] times 5, finishing with 72° C. 5 minutes. The 1123 bp product obtained was cut with BamHI and EcoRI and cloned into the vector pUC19 (Boehringer Mannheim). The DNA sequence was confirmed, using the Thermo Sequenase radiolabeled terminator cycle sequencing kit with [³³P] dideoxy nucleotides (Amersham Life Science, Amersham, UK). The construct was cloned into pET5c vector (Promega UK Ltd, Southampton, UK.) as a NdeI to EcoRI fragment (see *Molecular Cloning, A Laboratory Manual* eds. Sambrook J, fritsch E F, Maniatis T. Cold Spring Harbor Laboratory Press 1989, New York, USA). Plasmid DNA was prepared using Wizard® Plus SV Minipreps DNA purification System (Promega UK Ltd), or for larger scale, Qiagen Plasmid Midi Kit (Qiagen Ltd, Crawley, UK.). The new plasmid generated was named pET5c FLAG-αPs scAb.

The fos cassette was assembled by PCR of overlapping oligonucleotides:
Fos1for 5'-atggaattcctcgagaccgacacccta-caggcggaaaccgaccagctgga (SEQ ID NO: 15)
Fos80rev 5'-tcgcgatttcggtttgcagcgcg-gattttcgtcttccagctggtcggtt (SEQ ID NO: 16)
Fos 71for 5'-aaaccgaaatcgcgaacctgctgaaa-gaaaaagaaaagctggagttcatc (SEQ ID NO: 17)
Fos 155rev 5' ggaagcttgaattccgccggacggtgt-gccgccaggatgaactccagctt (SEQ ID NO: 18)

The above oligonucleotides were included in a reaction mix at 1 pmol each, and the reaction was driven using 10 pmol primers Fos1fS; 5'-atggaattcctcgagacc (SEQ ID NO: 19) and Fos 155rS 5'-ggaagcttgaattccgcc (SEQ ID NO: 20) using high fidelity polymerase and reaction components as previously. The resulting 155 bp product was digested with EcoRI, purified and cloned into EcoRI cut pUC19 for sequence analysis using standard procedures (see *Molecular Cloning, A Laboratory Manual* ibid). The Fos cassette was sub-cloned into the pET5c FLAG-αPs scAb plasmid as an XhoI-EcoRI fragment by substitution of the existing 320 bp XhoI-EcoRI fragment carrying the human constant region domain.

The 340 scAb was produced by substitution the VH and VK of the 340 antibody in place of the α-Ps VH and VK in ppM1His. The 340 VH was amplified with the primers 5'cagctgcaggagtctggggggaggcttag3' (SEQ ID NO: 21) (Genosys) and 5'tcagtagacggtgaccgaggttccttgacccagta3' (SEQ ID NO: 22) (Genosys). The reaction mixture included 0.1 μg template DNA, 2.6 units of Expand™ High Fidelity PCR enzyme mix, Expand HF buffer, 1.5 mM MgCl2,200 μM dNTPs and 25 pmoles of each primer. Cycles were 96° C. 5 minutes, followed by [95° C. 1 minute, 50° C. 1 minute, 72° C. 1 minute] times 5, [95° C. 45 seconds, 50° C. 1 minute, 72° C. 1 minute 30 seconds] times 8, [95° C. 45 seconds, 50° C. 1 minute, 72° C. 2 minutes] times 5, finishing with 72° C. 5 minutes. The 357 bp product was cut with PstI and BstEII and cloned into PstI and BstEII cut pPM1His (see *Molecular Cloning, A Laboratory Manual,* ibid). Similarly, the 340 VK was amplified with the primers 5'gtgacattgagct-cacacagtctcct3' (SEQ ID NO: 23) and 5'cagcccgttttatctc-gagcttggtccg3' (SEQ ID NO: 24) (Genosys). The 339 bp product was cut with SstI and XhoI and cloned into SstI and XhoI cut modified pPM1His (produced above). The DNA sequence was confirmed, using the Thermo Sequenase radiolabeled terminator cycle sequencing kit with [³³P] dideoxy nucleotides as before. DNA for the 340 scAb in the vector pPM1His was amplified with the primers RD 5' HIS: 5'gcggatcccatatgcaccatcatcaccatcaccaggtgcagctgcag3' (SEQ ID NO: 25) (Genosys) and RD 3' (given above) which introduced the 6 histidine residues at the 5' end and removed the 3' stop codon respectively. Reagents and conditions for amplification were exactly as for the α-Ps construct. The 1114 bp product obtained was cut with BamHI and EcoRI and cloned into the vector pUC19 (see *Molecular Cloning, A Laboratory Manual*, ibid). The DNA sequence was confirmed as before and the construct was cloned into pET5c vector as a NdeI to EcoRI fragment to generate the plasmid pEt5c HIS 340 scAb.

The jun cassette was assembled by PCR of overlapping oligonucleotides:

Jun1for 5'-atgagaattctcgagcg-tatcgctcgtctgtggaagaaaaagttaaaaccct (SEQ ID NO: 26)
Jun 85rev 5'-tagcggtggaagccagttcggagttct-gagctttcagggttttaactttt (SEQ ID NO: 27)
Jun 71for 5'-tggcttccaccgctaacatgctgcgt-gaacaggttgctcagctgaaacag (SEQ ID NO: 28)
Jun 146rev 5'-catgcgaattcgtggttcataactttct-gtttcagctgagcaacc (SEQ ID NO: 29)

The above oligonucleotides were included in a reaction mix at 1 pmol each, and the reaction was driven using 10 pmol primers Jun 1for-S; 5'-atgagaattctcgagcg (SEQ ID NO: 30) and Jun146rev-S; 5'-catgcgaattcgtggttc (SEQ ID NO: 31) using high fidelity polymerase and reaction components as previously. The resulting 146 bp product was digested with EcoRI, purified and cloned into EcoRI cut pUC19 for sequence analysis using standard procedures (see *Molecular Cloning, A Laboratory Manual* ibid) The Jun cassette was sub-cloned into the pEt$_5$c HIS 340 scAb plasmid as an XhoI-EcoRI fragment by substitution of the existing 320 bp XhoI-EcoRI fragment carrying the human constant region domain Plasmids his-340-jun and FLAG-αPs-fos, were used as templates for PCR using biotinylated primer BioT7; 5'-agatctcgatcccgcaaatta (SEQ ID NO: 32) and primer petrev;-5'-aaataggcgtatcacgaggcc (SEQ ID NO: 33). Primers were supplied by GenoSys (Cambridge, UK) and used in the reaction at a concentration of 1 pmol. Components and PCR conditions were as previously. The his-340-jun reaction product was 992 bp, and the FLAG-αPs-fos reaction product was 1002 bp. The products were purified using a spin purification cartridge (Qiagen, Crawley, UK) and diluted to 100 ng/µl concentration. Quantitation was by UV absorbance at 260 nm. 500 ng biotin labelled DNA was reacted with 10 µl streptavidin coated magnetic particles (Bangs labs, Fishers, USA). The reaction was conducted in a siliconised microcentrifuge tube in a volume of 500 µl PBS 1% (w/v) BSA for 10 minutes at room temperature. Following binding, the particles were collected by magnet (Dynal, Bromborough, UK) and washed three times using PBS 1% BSA.

Following the final wash, in vitro translation reaction was initiated by addition of 25 µl T7 Quick coupled transcription translation mix (Promega, Southampton, UK) supplemented with biotinyl lysine tRNA (Promega). The translation reaction was conducted at 30° C. for 60 minutes then placed on ice. Particles were collected by magnet, and washed using ice cold PBS containing 1% BSA.

In some experiments, non-magnetic steptavidin particles were used in IT reactions (Bangs Labs, Fishers, USA). In such cases particles were recovered during wash cycles by centrifugation.

In some experiments, coloured streptavidin particles, magnetic and non magnetic (Bangs Labs), were used in IVTT reactions.

In some experiments translation products bound to the particles were detected using antibodies for either the Flag or the his6 (SEQ ID NO: 34) epitope engineered into each of the model gene constructs. Antibodies were added to the washed particles diluted in PBS. Incubations were for 60 minutes at 4° C. with gentle mixing. A secondary reagent (anti-mouse-HRP conjugate) was added at the recommended dilution in PBS and incubated for a further 30 minutes at 4° C. Particles were washed three times using 200 µl PBS before colour development with the chromogenic substrate. Reactions were read at 492 nm.

Protein-protein binding reactions were conducted using IT proteins bound to the particle surface. In such experiments, non magnetic streptavidin particles were "captured" by protein mediated (fos:jun) binding to the surface of magnetic particles. Magnetic particles with fos IVTT product were mixed gently with non magnetic particles with jun bound on the surface. The reaction was conducted in 100 µl PBS, BSA and allowed to proceed at room temperature for 30 minutes. In a negative control reaction, non-magnetic particles with a Sca protein (α-Ps scAb; Molloy P et al., ibid) bound on the surface were mixed with the magnetic particles coated with the fos IVTT product. Following incubation, the particles were captured by magnet and washed six times using PBS, 1% BSA.

The presence of the captured target protein gene was confirmed using PCR and DNA sequencing. For detecting the jun model gene, jun specific primers Jun 1for-S and Jun146rev-S were used in a PCR assay. The assay was initiated by addition of 10% (v/v) particles directly into the PCR mix. Components and reaction conditions were as previously. The 146 bp jun specific product was detected by gel electrophoresis. For detecting the fos model gene, primers Fos1fS and Fos 155rS were used in a PCR assay. Reaction conditions and detection of the 155 bp fos specific product were as above. For detecting the negative control protein, primers Seq1scab 5'agatccctactataggta (SEQ ID NO: 35) and Seq2scab; 5'-ggtgagctcgatgtatcc (SEQ ID NO: 36) were used to detect a 115 bp product in the α-Ps scAb protein gene.

In the above experiments, Jun PCR products were detected following capture by fos magnetic particle under conditions were no α-Ps scAb PCR products could be detected following interaction with the fos magnetic particles.

EXAMPLE 2

In this example a single-chain antibody library was produced including unique peptide "barcodes". Human peripheral blood lymphocyte RNA was prepared according to standard procedures. Briefly, lymphocytes were prepared from 10 ml heparinised blood taken from 16 normal healthy donors. Lymphocytes were collected following a density gradient centrifugation procedure using Lymphoprep medium (Sigma, Poole, UK). RNA was prepared using the QuickPrep system and instructions provided by the supplier (Pharmacia, St Albans, UK). Synthesis of cDNA was conducted using a cDNA synthesis kit (Pharmacia, St Albans, UK) and random hexamer primers with conditions recommended by the supplier. Immunoglobulin heavy chain variable region (Vh) and light chain variable regions (Vl) were amplified from cDNA in separate PCR mixes using primer sets designed to maximise Vh and Vl repertoires. Primer sets were as described previously (Marks J. D. et al 1991, Eur. J. Immunol. 21: 985). Vh and Vl PCR reactions were conducted using, 2.6 units of Expand™ High Fidelity PCR enzyme mix (Boehringer Mannheim, Lewes, UK.), Expand HF buffer (Boehringer), 1.5 mM MgCl$_2$, 200 µM deoxynucleotide triphosphates (dNTPs) (Life Technologies, Paisley, UK) and 25 pmoles of each primer pool. Cycles were 96° C. 5 minutes, followed by [95° C. 1 minute, 50° C. 1 minute, 72° C. 1 minute] times 5, [95° C. 45 seconds, 50° C.

1 minute, 72° C. 1, minute 30 seconds] times 8, [95° C. 45 seconds, 50° C. 1 minute, 72° C. 2 minutes] times 5, finishing with 72° C. 5 minutes.

In a separate PCR, a linker fragment of form $(Gly_4Ser)_3$ (SEQ ID NO: 37) (Huston J. S. et al 1988, PNAS, 85: 5879-5883) was amplified from a cloned template pSW1-ScFvD1. 3 (McCafferty et al, 1990, Nature 348: 522-554) using primers sets detailed previously (Marks, J. D in Antibody Engineering, ed Borrebaek C.A.K New York O.U.P., 1995). The 93 bp linker fragment product was annealed together with an equimolar mixture of the Vh and Vl PCR products. The mixture was further amplified in a "pull through" reaction using flanking primers HuVH-BACKsfi and HuFORNot as detailed in Vaughan et al (Vaughan T. J. et al 1996, Nature Biotech. 14: 309-314). All fragments used in the pull-through reaction were purified free of their initial primers prior to inclusion in the reaction. Purification was conducted using the Wizard PCR Preps system from Promega (Promega, Southampton UK).

The assembled contig of form Vh-linker-Vl, was digested with restriction enzymes SfiI and NotI (Boehringer) using standard conditions and purified as above. The purified fragment was annealed with a double stranded synthetic oligonucleotide adapter mix designed to introduce a V8 protease cleavage site juxtaposed with a tract of randomised sequence in frame with the C-terminus of the Vl gene. This V8/unique sequence barcode was produced by annealing a pair of synthetic oligonucleotide pools of form 5'-ggccgc-gaggaagaggaa[(atg)/(can)/(agn)/(aan)/(gan)/(ttn)]2gc-3' (SEQ ID NO: 38) and 5'-qqccqc[(naa)/(ntc)/(ngt)/(nct)/(nag)/(cat)]$_2$ctccttctcctcgc-3' (SEQ ID NO: 39). This linker has NotI compatible ends (underlined) and therefore facilitates the insertion of the complete single chain antibody-V8/unique sequence barcode fragment into SfiI-NotI prepared pCANTAB 5 (Pharmacia) phagemid vector.

The unique sequence barcode was designed to avoid the introduction of stop codons and further biased to exclude encoding residues with greater than two alternative codons. By this strategy, the number of specific oligonucleotides required to identify a given de-coded peptide sequence, is minimised. In all, the unique sequence barcode is able to encode 11 of the 20 amino-acids. In addition to the V8 peptidase cleavage site (a string of 4 glutamic acid residues), the sequence barcode is 12 codons long. Thus from the repertoire of 11 amino acids (10 of which are encoded by either of two codons), is able to encode $11^{12}/2=\sim 1.5\times 10^{12}$ different peptides.

The assembled scfv fragment (Vh-linker-Vl) with SfiI and NotI prepared ends was annealed and ligated to the NotI sequence-barcode adapter and re-purified. For experiments expressing the human scfv library by phage display, the complete fragment was ligated into SfiI-NotI prepared pCANTAB 5 (Pharmacia) phagemid vector, and transformed into competent TG1 E. coli.

For other experiments using in vitro transcription and translation (IVTT), the assembled scfv library was subcloned into SfiI NotI prepared pCANTAB5-T7. This vector is the same as the commercially available pCANTAB5 except it was modified to include the T7 promoter sequence (ttaatacgactcactata) (SEQ ID NO: 40) inserted at the HindIII site at position 2235. The modification was achieved by ligation of a double-stranded synthetic DNA linker of sequence 5'-agctaatacgactcactata (SEQ ID NO: 41) into HindIII cut and de-phosphorylated pCANTAB5. Recombinant clones containing the T7 promoter were selected using a diagnostic PCR.

Following ligation and transformation into competent TG1 E. coli, cells were grown for 1 hour in 1 ml of SOC medium and then plated onto TYE medium with 100 ug/ml ampicillin. Colonies were scraped off plates into 5 ml of 2×TY broth containing ampicillin. The cultured library was used to prepare DNA for IVTT reactions.

The pCANTAB5-T7 Scfv library DNA was used in an in vitro translation reaction. The IVTT was conducted using the T7 Quick coupled transcription translation mix (Promega, Southampton, UK) and 10 μg of the pCANTAB5-T7 Scfv library DNA in a total volume of 50 μl. The translation reaction was conducted at 30° C. for 90 minutes then placed on ice. In some experiments reactions were monitored for the presence of translation products using $^{35}$S-methionine incorporation assays. Reactions were stored at −70° C. prior to use in binding and screening assays.

The single-chain antibody library was used to in a binding reaction to recombinant human p53 protein (Oncogene Research Products-Calbiochem, Nottingham, UK). The IVTT mix was diluted ×10 fold in PBS and used in a binding assay to human recombinant p53 protein immobilised in a 96-well microplate. The p53 protein was immobilised by overnight incubation at a concentration of 100 μg/ml in phosphate buffer at 4° C. The plate was washed using PBS 0.5% (w/v) BSA and the diluted IVTT mix added to the test and control wells for binding. The binding reaction was conducted at 37° C. for 90 minutes. The plate was washed ×3 using PBS-T (PBS+0.05% v/v tween-20) and subjected to V8 protease digestion (Takara, Wokingham, UK). Protein fragments were collected from the supernatant and size fractionated to exclude the V8 protease and other large species before analysis by MALDI-tof MALDI-tof fragment analysis identified a number of peptide fragments. The peptide sequences were used to design a set of corresponding synthetic oligonucleotides. The oligonucleotides were used in a PCR based screen of the single chain library. Pfu turbo (Stratagene Europe) DNA polymerase was used to synthesise complementary strands in members of the human single-chain antibody library DNA. Following 15 rounds of thermal cycling, the product was subjected to DpnI digestion. This step depleted the mixture of parental plasmid molecules to ensure that only the newly synthesised primed products were propagated. 1 μl of the reaction was transformed into TG1 competent cells and plated onto LB plates containing 100 μg/ml ampicillin. Individual clones were picked, expanded and DNA prepared according to standard procedures. The DNA was used directly in a second round of screening involving IVTT, antigen binding, V8 protease digestion, MALDI-tof fragment analysis. After 2 rounds of selection 6 scFv's were isolated which bound recombinant p53.

EXAMPLE 3

The experiments described in the present example were conducted using an Fab expression vector pC5A8-03, the construction of which is as follows. The vector pC5A8-01 is based on the vector pLITMUS28 (New England Biolabs, MA. USA) which provides an inducible lac promoter and a M13 origin of replication. The Fab region of the antibody was assembled from two DNA fragments encoding the variable region (VH) and first constant region (CH1) of the heavy chain and the variable region (VK) and constant region (CK) of the kappa light chain of a humanised monoclonal antibody 5A8 directed against CD4 (Reimann K A. et al., Aids research and human retroviruses 13, 11: p933, 1997). These fragments were fused to the pelB leader sequence (Lei S-P. et al. Journal of Bacteriology, 169: 9: 4379-4383, 1987) and inserted between the BglII and Bst98I restriction sites of pLITMUS28 as described below. All following molecular biology procedures will be familiar to those skilled in the art and can be found in Molecular Cloning, A Laboratory Manual eds. Sambrook J., Fritsch E F. and Maniatis T. Cold Spring Harbor Laboratory Press 1989, New York, USA. All oligonucleotides were synthesised by Genosys Biotechnologies Europe Ltd., Cambridge, UK. Unless otherwise stated, all restriction endonucleases were purchased from Life Technologies, Paisley, UK). All polymerase chain reactions were carried out using pfu DNA polymerase (Promega, Southampton, UK).

In order to assemble the light chain fragment, the pel B leader sequence was amplified using the polymerase chain reaction (PCR), using a Hybaid Touchdown Thermal Cycler, from clone pPM1-HIS which contains a single-chain antibody fragment (scAb) against *Pseudomonas aeruginosa* (Molloy, P. et al. Journal of Applied Bacteriology, 78: 359-365, 1995). This initial reaction was carried out using oligonucleotides OL001 which encodes a BglII restriction site, the N terminal residues of the pelB leader sequence and the Shine Dalgarno sequence and OL002 which encodes the C-terminus of the pel B leader and the N-terminal residues of a kappa light chain from pDIVKV3 (ref). The product of this reaction was purified from NuSieve GTG agarose (Flowgen, Lichfield, UK) using a Wizard® PCR purification kit (Promega UK Ltd., Southampton, UK) denatured and used, in conjunction with OL004 which encodes the junction of the variable and constant regions of the kappa light chain, to amplify the variable region of the kappa chain from clone pDIVKV3, by PCR using standard protocols. The constant region of the kappa light chain was amplified, by PCR, from clone pPM1-HIS (Molloy et al.) using OL003 which encodes the C-terminal residues of the variable region and the N-terminal residues of the constant region and OL005, which encodes the C-terminal residues of the constant regions of the kappa light chain and the restriction enzyme site EcoR1. These two fragments were subsequently amplified by overlap PCR using OL001, and OL005, digested with BglII and EcoRI and cloned into pLITMUS28 in order to produce pC5A8-01.

The heavy chain was assembled by amplification of the pel B leader sequence from the assembled light chain using OL006, which encodes an EcoRI site and the Shine Dalgarno sequence and OL007, which encodes the C-terminal residues of the pel B leader sequence and the N-terminal residues of a heavy chain from pDIHV4. The product of this reaction was used, alongside OL009, which encodes the junction of the variable and constant regions of the heavy chain, to amplify the variable region of the IgG1 heavy chain from clone pDIHV4. Exon 1 of the heavy chain constant region was amplified, by PCR from clone pSV gptHuIgG1 using OL008 and OL010, which encode the C-terminal residues of the variable regions of the heavy chain and the N-terminus of the constant chain (OL008) and the C-terminal residues of exon 1 and the restriction site for SstI (OL010). The products of these reactions were amplified by overlap PCR using OL006 and OL010, digested with EcoRI and SStI and cloned into pLITMUS28 containing the light chain fragments in order to produce pC5A8-02.

The C-terminal residues of CHI and a C-terminal FLAG tag sequence (DYKDDDDK) (SEQ ID NO: 42) (Knappik A. and Pluckthun A. Biotechniques, 17; 754-761, 1990) were added using OL011 and OL012 which included the restriction sites Eco/CRI and Bst98I in order to produce pC5A8-03. Alternatively, these tags could include the 6HIS tag (SEQ ID NO: 34) or MS tags (see example).

The oligonucleotides utilised in the production of pC5A8-0, pC5A8-02 and pC5A8-03 are listed below;

OL001; 5' GGGCAGATCTTTMCTTTAAGAAG-GAGATATACATATGAAATACCTATTGCCTACGG 3' (SEQ ID NO: 43)

OL002; 5' GGGTCTGGGTCATAACGATATCGGC-CATCGCTGGTTGGGCAGC 3' (SEQ ID NO: 44)

OL003; 5' GGTACCAAACTGGAGATCAAACGGACT-GTGGCTGCACCATCT 3' (SEQ ID NO: 45)

OL004; 5' AGATGGTGCAGCCACAGTC-CGTTTGATCTCCAGTTTGGTACC 3' (SEQ ID NO: 46)

OL005; 5' GATCGAATTCCTMCACTCTCCGCGGT-TGAAGCTCTTTG 3' (SEQ ID NO: 47)

OL006; 5' GATCGAATTCTAACUTMGAAG-GAGATATACATATG 3' (SEQ ID NO: 48)

OL007; 5' GGACTGMCCAGTTGGACTTCGGC-CATCGCTGGTTGGGCAGC 3' (SEQ ID NO: 49)

OL008; 5' ACCCTGGTTAcCGTCTCCTCAGCCTC-CACCAAGGGCCCATC 3' (SEQ ID NO: 50)

OL009; 5' GATGGGCCCTTGGTGGAGGCTGAG-GAGACGGTMCCAGGGTAC 3' (SEQ ID NO: 51)

OL010; 5' GATCGAGCTCTGCTTTCTTGTCCACCT-TGGTGTTGC 3' (SEQ ID NO: 52)

OL011; 5' CCCAAATCTTGCGCTGCAGACTACMA-GACGACGACGACMATAGCTCGAGC 3' (SEQ ID NO: 53)

OL012; 5' TTMGCTCGAGC-TATTTGTCGTCGTCGTCTTTGTAGTCTG-CAGCGCAAGAMGGG 3' (SEQ ID NO: 54)

The production of functional Fab was demonstrated by ELISA. In summary, the above vector was transferred into *E. coli* strain DH5α and grown at 37° C. in the presence of 100 μg/ml ampicillin and 1% glucose until an $OD_{600}$ of 0.5 was attained. Protein production was induced by the addition of 1 mM isopropylthio-βD-galactoside (IPTG) in the absence of glucose. The periplasmic fraction was released by osmotic shock using 30 mM Tris HCl 20% sucrose pH8.0, 1 mM EDTA followed by 5 mM $MgSO_4$ (Molloy, P. et al. Journal of Applied Bacteriology, 78: 359-365, 1995) and added directly to an Immulon 4 ELISA plate (Dynex,) which had previously been coated overnight with soluble human CD4 (Intracel Corp., Issaquah, Wash.) at a concentration of 1 μg/ml in phosphate buffered saline (PBS) pH7.4, at room temperature in a humidified chamber. Alternatively, the periplasmic fraction could be released by cell lysis or by the addition of 1 mM EDTA. Non specific binding was reduced by incubating the plate for 1 hour at room temperature with PBS containing 0.05% Tween 20, 2% bovine serum albumin (BSA) and 0.05% thimerosal (Sigma) prior to addition of the soluble Fab. The anti-CD4 specific Fab was detected using goat anti-human IgG Fab specific Horseradish peroxidase conjugate (Sigma, UK) which was itself detected using 5, 5' tetramethylbenzidine dihydrochloride (TMB)(Sigma, UK) and hydrogen peroxide in phosphate/citrate buffer pH5.0. Colour development was stopped after 30 minutes using $0.2NH_2SO_4$ and the absorbance monitored at 450 nm. Alternatively ABTS/citrate (Sigma, UK) could be used for detection.

In order to produce a library of CDR3 sequences, unique restriction sites were introduced into vector pC5A8-03 by oligonucleotide-directed mutagenesis (Kunkel TA. Proc. Natl. Acad. Sci. USA: 488-492 (1985) and Current Protocols in Molecular Biology eds. Ausubel F M, Brent R., Kingston R E., Moore D D., Seidman J G., Smith J A., Struhl K. John Wiley & Sons, Inc.) using the oligonucleotides listed below. The presence of the AatII and HindIII (5' and 3' to LCDR3) and BssHII and SanDI (5' and 3' to HCDR3) restriction sites in the kappa light chain and the heavy chain respectively, were confirmed by digestion with the appropriate restriction enzymes. These plasmids, each containing an additional restriction site, were designated pC5A8-04 to pC5A8-07.

OL013; 5' GMGACGTCGCTGTTTAC 3' (SEQ ID NO: 55)

OL014; 5' GGTACCMGCTTGAGATC 3' (SEQ ID NO: 56)

OL015; 5' CTACTGCGCGCGTGAAAAAG 3' (SEQ ID NO: 57)

OL016; 5' GGGTCAGGGGACCCTGG 3' (SEQ ID NO: 58)

Following digestion of pC5A8-07 with AatII and HindIII, the highly variable residues in CDR3 of the kappa light chain variable regions were randomised using a mixture of degenerate oligonucleotides carrying the anchor residues (aa 83-88 and aa 97-103) and an 10 nucleotide palindromic sequence at their 3' end which encompasses the restriction endonuclease site for HindIII. These oligonucleotides hybridise at their 3' ends and then act as a substrate for DNA polymerase resulting in the production of double-stranded homoduplex, which is digested with the two restriction enzymes and cloned into the digested vector using standard protocols (see Current Protocols in Molecular Biology eds. Ausubel F M., Brent R., Kingston R E., Moore D D., Seidman J G., Smith J A., Struhl K John Wiley & Sons, Inc.) The oligonucleotides were prepared such that residues 91, 92, 93, 94, 95, 95A, 95B and 96 were randomised by the inclusion of equal concentrations of each nucleotide at each step of the oligonucleotide synthesis (Genosys, Cambridge, UK).

The sequence of the mutagenic oligonucleotides is based on a CDR3 length of 10 residues. Residues 89 and 90 are relatively conserved and are therefore fixed in this example. The residues to be randomised are shown in italics. Additional libraries with a CDR3 of 6, 7, 8 or 9 residues can also be created by varying the length of the randomised region.

Positive strand; 5'
GAAGACGTCGCTGTTTACTACTGCCAG-CAGNNSNNSNNSNNSNNSNNSNNSACCTTCG GTG-GTGGTACCAAGCTTGG 3' (SEQ ID NO: 59)

Negative stand: 5'
CCMGCTTGGTACCACCACCGMG-GTSNNSNNSNNSNNSNNSNNSNNCTGCTGGCAGT AGTAAACAGCGACGTCTTC 3' (SEQ ID NO: 60)

CDR3 of the heavy chain was randomised using the restriction endonuclease sites BssHII and SanDI and the mutagenic oligonucleotides listed below, in a similar manner to that described in the previous section. In this case residues 95-100D are randomised. the residues to be randomised are shown in italics. Additional libraries with a CDR3 of 9, 11 or 12 residues can also be created by varying the length of the randomised region.

Positive strand; 5'
CTACTGCGCGCGT-NNSNNSNNSNNSNNSNNSNNSNNSNNSNNSTTCGC-TACTGGGGT CAGGGGACCCCT (SEQ ID NO: 61)

Negative stand: 5'
AGGGGTCCCCTGACCCCAGTMGC-GAASNNSNNSNNSNNSNNSNNSNNSNNSNNSNNA CGCGCGCAGTAG 3' (SEQ ID NO: 62)

A library in which both the heavy and light chains contained a randomised CDR3 was produced by carrying out both the heavy and light chain mutagenesis methods described above.

In order to increase the efficiency of selection of high affinity binders, the FLAG tag mentioned above was replaced with a mass tag using the restriction endonucleases PstI and XhoI. In order to increase the library size further two tags can be used. In this case the tags must differ in length by at least two residues in order to be distinguished following the removal of tags 1 and 2 with a protease such as Factor Xa The oligonucleotides were designed with a palindromic sequence at their 3' end which encompass the restriction endonuclease site for XhoI. The oligonucleotides hybridise at their 3' ends and then act as a substrate for DNA polymerase resulting in the production of double-stranded homoduplex, which is digested with the two restriction enzymes Pst1 and XhoI and cloned into the digested vector using standard protocols (see Current Protocols in Molecular Biology eds. Ausubel F M., Brent R., Kingston R E., Moore D D., Seidman J G., Smith J A., Struhl K John Wiley & Sons, Inc.).

As an example a tag of 8 residues can be created using the oligonucleotide 5' NAC NCC NGG NTG TKC VAG GNV CNT 3' (SEQ ID NO: 2). The length of this Tag is increased to 11 residues if a second tag of 8 residues is also included due to the incorporation of the site for protease Factor Xa, which is shown in italics. This allows the tags to be identified as tag 1 or tag 2 following their removal and analysis by mass spectroscopy.

Single tag.

Forward Oligo; 5' GCG CTG CAG GAY GGN CGN NAC NCC NGG NTG TKC VAG GNV CNT TAG CTC GAG CTA 3' (SEQ ID NO: 63)

Reverse Oligo; 5' TAG CTC GAG CTA ANG BNC CTB GMA CAN CCN GGN GTN CCG CCC GTC CTG CAG CGC 3' (SEQ ID NO: 64)

Double tag.

Forward Oligo; 5' GCG CTG CAG GAY GGN CGN NAC NCC NGG NTG TKC VAG GNV CNT GAY GGN CGN NAC NCC NGG NTG TKC VAG GNV CNT TAG CTC GAG CTA 3' (SEQ ID NO: 65)

Reverse Oligo; 5' TAG CTC GAG CTA ANG BNC CTB GMA CAN CCN GGN GTN CCG CCC GTC ANG BNC CTB GMA CAN CCN GGN GTN CCG CCC GTC CTG CAG CGC 3' (SEQ ID NO: 66)

EXAMPLE 4

In order to select high affinity binders, the initial library was transferred into *E. coli* DH5a by electroporation (Bio-rad) and plated onto L agar containing 100 µg/ml ampicillin and 1% glucose and incubated at 37° C. overnight. The transformed cells were harvested and used to inoculate a fresh batch of L broth containing 100 µg/ml ampicillin. The remainder of the library should be retained and stored at −70° C. and used as starting material for the rescue of high affinity clones, as described later. The newly inoculated cultures were incubated for 2 hours at 37° C. prior to the addition of isopropylthio-β-D-galactoside (IPTG) to a final concentration of 0.1mM. The cultures were then incubated at 37° C. for a further 3 hours.

100 ml cultures of bacteria producing the soluble Fab library were centrifuged at 4000 rpm for 20 minutes at 4° C. and the resulting pellet resuspended in phosphate buffered saline containing 1 mM EDTA. Following agitation for 5-20 minutes on ice, the EDTA permeabilises the outer membrane and allows the periplasmic contents to leak out. The supernatant was then clarified by centrifugation and the supernatant used in subsequent steps. Alternative protocols for the release of the periplasmic contents could also be utilised (Molloy, P. et al. Journal of Applied Bacteriology, 78; 359-365, 1995 and Molecular Cloning, A Laboratory Manual eds Sambrook J., Fritsch E F. and Maniatis T. Cold Spring Harbor Laboratory Press 1989, New York, USA).

The periplasmic extract, containing the Fab library was aliquoted into Nunc-immunotubes which had been coated overnight with soluble human CD4 (Intracel Corp., Issaquah, Wash.) at a concentration of 1 µg/ml in phosphate buffered saline (PBS) pH7.4, at room temperature in a humidified chamber. Non specific binding was reduced by incubating the tubes for 1 hour at room temperature with PBS containing 0.05% Tween 20, 2% bovine serum albumin (BSA) and 0.05% thimerosal (Sigma) prior to addition of the soluble Fab. After allowing the Fab to bind to the CD4 antigen for 1 hour at room temperature, the unbound Fab was eliminated by washing the tubes 20 times with PBS, 0.05% Tween 20.

In order to identify the amino acid sequence of those Fabs which remain bound, the mass tag was removed with Factor Xa using standard protocols. The mass tag was then analysed by MALDI-TOF (MS/MS) spectrometry in which the molecular weight of each tag was determined then the sequence information obtained by analysis of the secondary ionisation events. By combining this information the amino acid sequence of the tags could be assigned.

In some instances it may be necessary to increase the efficiency of protease cleavage by eluting the bound Fab, neutralising and purifying the Fab from the other *E. coli* proteins by affinity purification using a sepharose-anti Ck column (Pierce Warriner, Cheshire, UK) prepared according to the manufacturers instructions. The mass tag can then be removed from the bound Fab using Factor Xa Following the identification of the mass tag, a further two oligonucleotides were produced. The 3' oligonucleotide encodes the sequence of the mass tag while the 5' oligonucleotide is OL001 which encodes the sequence at the N-terminus of the Fab.

Positive stand; 5' GG GCA GAT CTT TM CTT TM GM GGA GAT ATA CAT ATG MA TAC CTA TTG CCT ACG G 3' (SEQ ID NO: 43)

Negative strand; 5' TAG CTC GAG CTA ANG BNC CTB GMA CAN CCN GGN GTN CCG CCC GTC ANG BNC CTB GMA CAN CCN GGN GTN CCG CCC GTC CTG CAG CGC 3' (SEQ ID NO: 66)

The clone containing the high affinity binder was rescued by adding 10 µl of the *E. coli* library to a PCR reaction containing the oligonucleotides described above. The conditions required for this reaction may vary depending upon the oligonucleotides being utilised. Following amplication, the PCR product was sequenced and subsequently purified from low melting point agarose, digested with AatII, which occurs at the N-terminus of CDR3 of the kappa light chain and SanDI, which occurs at the C-terminus of CDR3 of the heavy chain in vector pC5A8-07 and transferred into vector pC5A8-07 which had been digested with the same restriction endonucleases, using standard protocols (see Molecular Cloning, A Laboratory Manual eds Sambrook S., Fritsch E F. and Maniatis T. Cold Spring Harbor Laboratory Press 1989, New York, USA). The resulting plasmid was transferred into *E. coli* DH5a by electroporation using standard protocols and stored at −70° C. Alternatively, the product of the PCR reaction could be digested with a number of alternative restriction endonucleases and transferred into alternative vectors for Fab expression.

In some cases a number of mass tags may be present following the initial round of panning. In this case, a library of clones are amplified from the stored library using a mixture of 3' oligonucleotides. This limited library can then be subjected to further rounds of panning, the bound clones can be re-analysed by MALDI-TOF and the sequence of the internal tags used to create a limited repertoire of PCR primers.

In order to confirm the affinity of the selected anti-CD4 specific Fab, periplasmic extracts should be prepared as described above and used immediately in a CD4 specific ELISA. The apparent affinity is a combination of the actual affinity and the concentration of the Fab therefore the concentration of the Fab should be established by carrying out an additional capture ELISA on the same extract in which a standard concentration curve is produced against the FLAG tag or the human Ck domain (McGregor D P., Molloy P E., Cunningham C. and Harris W J. Molecular Immunology 31, 219-116. 1994).

EXAMPLE 5

In this example, human p53 protein was modified with a chemical tag at its N terminus, cleaved with a protease, the chemically tagged peptide then recovered using a tag-specific monoclonal antibody and the peptide then analysed by MALDI-ToF. p53 protein was a gift from Dr Borek Vojisek (University of Brno, Czech Republic). 100 ug of p53 protein with the succinimide ester of (methyl sulphonyl) ethyl carbonate according to Mikolajczyk et al., *Bioconjugate Chem.*, vol 7 (1996) p150-158 in order to block lysine side-chains. The blocked protein was dissolved at 1 mg/ml in 0.1M sodium bicarbonate buffer pH8.5 and NHS-SS-biotin (Pierce, Chester, UK) was added to 100 ug/ml final. The reaction was carried out for 6 hours at room temperature and terminated with ethanolamine. The protein mixture was then passed down a Sephadex G25 column (Pharmacia, Milton Keynes, UK) in PBS and the void volume collected using A280 measurements of the eluates. 40 ul of eluate containing 2 ug p53 was then heat denatured (95c for 5 mins), cooled to 37c and 1 ug endoproteinase Arg-C (from *C. histolyticum*, Calbiochem, Nottingham, UK) was added and the mixture incubated at 37c for 1 hour. Then 10 ul of streptavidin-agarose (Sigma, Poole, UK) in PBS was added and the mixture shaken for 10 minutes. The agarose was pelleted at 16000 g for 1 min and washed three times in TSO buffer (75 mM Tris.HCl, 200 mM NaCl, 0.5% N-octyl glucoside, pH8) and three times in TSMK (10 mM Tris.HCl, 200 mM NaCl, 5 mM 2-mercaptoethanol, pH8). Finally, 10 ul of a saturated solution of alpha-cyano-4-hydroxycinnamic acid in 1% aqueous trifluoroacetic acid/acetonitrile (1:1 v/v) was added to the washed beads and 1 ul of this was loaded onto the mass spectrometer chip. The analysis was carried out using a Perseptive Biosystems Voyager-DE STR Biospectrometry Workstation (Perseptive Biosystems). The mass spectra were collected by adding spectra from 200 laser shots.

The results showed a major peak corresponding to the 65 amino acid N terminal Arg-C endoprotease fragment with no significant levels of other p53 Arg-C peaks.

EXAMPLE 6

The method of example 5 was repeated except that the N terminal biotin-tagged peptide was used to isolate a single-chain Fv antibody fragment from a phage display library of single-chain Fv's. Subsequently, the single-chain Fv was used to isolate the N-terminal peptide fragment from a protease digest of the test protein as confirmed by MALDI-ToF. An extract of normal human brain, prepared as in example 4, was conjugated to KLH according to Harlow and Lane, "Antibodies" (1988) (Cold-Spring Harbor Publications) and used to immunise two BalbC mice. 2 doses were given intra-peritoneally with an interval of 4 weeks between them. 3 to 4 days after the 2nd inoculation, the mice were sacrificed and spleens removed by dissection. Spleen mRNA preparation was then initiated using QuickPrep™ mRNA purification kit (Pharmacia) according to the manufacturer's instructions The Pharmacia Recombinant Phage Antibody System (Pharmacia) was used to produce a library of mouse single chain Fvs (ScFv). First-strand cDNA was generated from the mRNA using M-MuLV reverse transcriptase and random hexamer primers. Antibody heavy and light chain genes were then amplified using specific heavy and light chain primers complementary to conserved sequences flanking the antibody variable domains. The 340 and 325 base pair products generated for heavy and light chain DNA respectively were separately purified following agarose gel electrophoresis. These were then assembled into a single ScFv construct using a DNA linker-primer mix to give the VH region joined by a (Gly4Ser)3 (SEQ ID NO: 37) peptide to the VL region. The assembled ScFv were amplified with primers designed to insert Sfi 1 and Not 1 sites at the 5' and 3' ends respectively, giving an 800 bp product. This fragment was purified, sequentially digested with SfiI and NotI, and repurified. The fragment was then ligated into SfiI and NotI cut pCANTAB 5 phagemid vector. PCANTAB 5 contains the gene encoding the Phage Gene 3 protein (g3p) and the ScFv is inserted adjacent to the g3 signal sequence such that it will be expressed as a g3p fusion protein. Competent *E. coli* TG1 cells were transformed with the pCantab 5/ScFv phagemid then subsequently infected with the M13KO7 helper phage. The resulting recombinant phage contained DNA encoding the ScFv genes and displayed one or more copies of recombinant antibody as fusion proteins at their tips.

Phage-displayed ScFv that bind to the peptides were then selected or enriched by panning. Briefly, the biotinylated and protease treated p53 preparation from example 1 was applied to a streptavidin-coated glass slide (Radius Biosciences, Waltham, USA) and the slide was washed four times in PBS. After blocking with 2% non-fat dry milk in PBS, the phage preparation was applied and incubated for 1 hour. After washing 10 times with TBS/0.05% Tween 20, peptide reactive recombinant phage were detected with horse radish peroxidase conjugated anti-M13 antibody and revealed with o-phenylene diamine chromogenic substrate. These phage were subsequently eluted with 0.1M glycine-.HCl pH2.2 and 1 mg/ml BSA and neutralised with 2M Tris base. The eluted phage were amplified in JM103 grown in 25 ml J broth. Two additional rounds of panning were undertaken and finally 10 single plaques were isolated, pooled and further amplified. An aliquot of $10^{10}$ amplified phage was incubated for 2 hours at 4c with 0.1 ug of biotinylated and endoproteinase Arg-C digested p53 in TSO buffer. After 2 hours, 0.5 ug of anti-M13 (Pharmacia) in TSO was added and incubated for 1 hour following which 5 ul of protein A/G agarose (Sigma) was added and the mixture incubated for a further 0.5 hours with swirling. The agarose beads were then pelleted, washed as in example 1 above and analysed by mass spectrometry.

The results showed the same major peak as in example 1 corresponding to the 65 amino acid N terminal Arg-C endoprotease fragment.

EXAMPLE 7

In this example, a gene fragment encoding a test protein was subjected to priming with a synthetic oligonucleotide encoding a polyhistidine tag. The cDNAs were expressed by in vitro transcription and translation (IVTT) and the tagged peptide fragments were then isolated using a nickel chelate column. These fragments were then used to isolate a single-chain Fv antibody fragment. Subsequently, the single-chain Fv was used to isolate a peptide fragment from a protease digest of the test protein as confirmed by mass spectrometry.

EXAMPLE 8

The method of example 6 was repeated using a total protein preparation from cells and the chemically tagged peptide were used to isolate a collection of single-chain Fv antibody fragments. Subsequently, a mixture of twelve of these single-chain Fv's was used to isolate peptide fragments from a protease digest of the test protein and analysed by mass spectrometry.

---

I claim:

1. A method of identifying a recombinant antibody or antibody domain which binds to an antigen of interest, comprising:
   (i) providing an antibody library, wherein each antibody member comprises within its amino acid sequence or terminal to it, one or more individual identifier sequence amino acid tracts which is unique to said antibody and wherein said sequence is further flanked by one or more protease sensitive sites;
   (ii) contacting said antibody of the library with one or more of said antigens to form an antigen-antibody complex,
   (iii) isolating the antigen-antibody complex of (ii),
   (iv) digesting said antigen-antibody complex to cleave the protease sensitive sites and release said individual identifier sequence tract(s), and
   (v) determining said released sequence tract(s) and using such sequence information to recover the individual antibody member from the library, and (vi) optionally repeating each of (ii) to (v) iteratively for screening and enrichment for an antibody which binds to the antigen of interest, wherein
said protease sensitive site is the site for enterokinase, Factor Xa digestion, or endoprotease digestion,
said antibody domain is an Fv domain comprising a VH and VL chain, and
said identifier sequence tract is C-terminal to the Fv domain.

2. A method according to claim 1, wherein determination of the released identifier sequence tract(s) is achieved by mass spectrometry.

3. A method of claim 1, wherein the mass spectrometry is matrix-assisted laser desorption/ionization time-of-flight (MALDI-ToF) spectrometry.

\* \* \* \* \*

SEQUENCE LISTING

```
<160> NUMBER OF SEQ ID NOS: 66

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 1

Asp Asp Asp Asp Lys
1               5

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(24)
<220> FEATURE:
<221> NAME/KEY: modified_base
<222> LOCATION: (1)
<223> OTHER INFORMATION: a, c, g or t
<220> FEATURE:
<221> NAME/KEY: modified_base
<222> LOCATION: (4)
<223> OTHER INFORMATION: a, c, g or t
<220> FEATURE:
<221> NAME/KEY: modified_base
<222> LOCATION: (7)
<223> OTHER INFORMATION: a, c, g or t
<220> FEATURE:
<221> NAME/KEY: modified_base
<222> LOCATION: (10)
<223> OTHER INFORMATION: a, c, g or t
<220> FEATURE:
<221> NAME/KEY: modified_base
<222> LOCATION: (20)
<223> OTHER INFORMATION: a, c, g or t
<220> FEATURE:
<221> NAME/KEY: modified_base
<222> LOCATION: (23)
<223> OTHER INFORMATION: a, c, g or t

<400> SEQUENCE: 2 nac ncc ngg ntg tkc vag gnv cnt                                        24
Xaa Xaa Xaa Xaa Xaa Xaa Xaa Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Asn, Asp, His or Tyr
<220> FEATURE:
<221> NAME/KEY: MOD_RES
<222> LOCATION: (2)
<223> OTHER INFORMATION: Thr, Pro, Ala or Ser
<220> FEATURE:
<221> NAME/KEY: MOD_RES
<222> LOCATION: (3)
<223> OTHER INFORMATION: Arg, Gly or Trp
<220> FEATURE:
<221> NAME/KEY: MOD_RES
<222> LOCATION: (4)
<223> OTHER INFORMATION: Leu, Met or Val
<220> FEATURE:
<221> NAME/KEY: MOD_RES
<222> LOCATION: (5)
<223> OTHER INFORMATION: Phe or Cys
<220> FEATURE:
<221> NAME/KEY: MOD_RES
<222> LOCATION: (6)
<223> OTHER INFORMATION: Gln, Glu or Lys
```

```
<220> FEATURE:
<221> NAME/KEY: MOD_RES
<222> LOCATION: (7)
<223> OTHER INFORMATION: Asp, Val, Ala, Gly or Glu
<220> FEATURE:
<221> NAME/KEY: MOD_RES
<222> LOCATION: (8)
<223> OTHER INFORMATION: His, Leu, Pro or Arg

<400> SEQUENCE: 3

Xaa Xaa Xaa Xaa Xaa Xaa Xaa Xaa
1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Glu Gly Arg
1

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Gly Ala Ala His Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Val Pro Arg Gly Ser
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Asp Asp Asp
1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 8

Pro Gly Ala Ala His
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Val Pro Arg
1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Val Pro Arg Gly
1               5

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Gly Lys Ser Ser Gly Ser Gly Ser Glu Ser Lys Val Asp
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Asp Tyr Lys Asp Asp Asp Lys
1               5

<210> SEQ ID NO 13
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggatccca tatggactac aaagacgatg acgacaaaca ggtgcagctg cag          53

<210> SEQ ID NO 14
<211> LENGTH: 35
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
gcgaattcgt ggtggtggtg gtggtgtgac tctcc                              35

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atggaattcc tcgagaccga caccctacag gcggaaaccg accagctgga              50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcgcgatttc ggtttgcagc gcggattttt cgtcttccag ctggtcggtt              50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaaccgaaat cgcgaacctg ctgaaagaaa aagaaaagct ggagttcatc              50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggaagcttga attccgccgg acggtgtgcc gccaggatga actccagctt              50

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atggaattcc tcgagacc                                                 18

<210> SEQ ID NO 20
<211> LENGTH: 18
<212> TYPE: DNA
<213> ORGANISM: Artificial Sequence
<220> FEATURE:
```

-continued

<223> OTHER INFORMATION: Description of Artificial Sequence: Synthetic
      primer

<400> SEQUENCE: 20
ggaagcttga attccgcc                                                   18

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagctgcagg agtctggggg aggcttag                                        28

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcagtagacg gtgaccgagg ttccttgacc ccagta                               36

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgacattga gctcacacag tctcct                                          26

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cagcccgttt tatctcgagc ttggtccg                                        28

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcggatccca tatgcaccat catcaccatc accaggtgca gctgcag                   47

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
atgagaattc tcgagcgtat cgctcgtctg gaagaaaaag ttaaaaccct          50

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tagcggtgga agccagttcg gagttctgag ctttcagggt tttaactttt          50

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggcttccac cgctaacatg ctgcgtgaac aggttgctca gctgaaacag          50

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
catgcgaatt cgtggttcat aactttctgt ttcagctgag caacc              45

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atgagaattc tcgagcg                                             17

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
catgcgaatt cgtggttc                                            18

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 32
agatctcgat cccgcaaatt a                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aaataggcgt atcacgaggc c                                              21

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 34

His His His His His His
1               5

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agatccctac tataggta                                                  18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggtgagctcg atgtatcc                                                  18

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser Gly Gly Gly Gly Ser Gly Gly Gly Gly Ser
1               5                   10                  15

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (19)..(24)
<223> OTHER INFORMATION: This region may encompass 'atgatg', 'cancan',
      'agnagn', 'aanaan', 'gangan' or 'ttnttn' wherein n is a, c, g,
      or t

<400> SEQUENCE: 38
ggccgcgagg aagaggaann nnnngc                                            26

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: This region may encompass 'naanaa', 'ntcntc',
      'ngtngt', 'nctnct', 'nagnag' or 'catcat' wherein n is a, c, g,
      or t

<400> SEQUENCE: 39
ggccgcnnnn nnctccttct cctcgc                                            26

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ttaatacgac tcactata                                                     18

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
agctaatacg actcactata                                                   20

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Tyr Lys Asp Asp Asp Asp Lys
1               5

<210> SEQ ID NO 43
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 43
gggcagatct ttaactttaa gaaggagata tacatatgaa atacctattg cctacgg      57

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gggtctgggt cataacgata tcggccatcg ctggttgggc agc                    43

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggtaccaaac tggagatcaa acggactgtg gctgcaccat ct                     42

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
agatggtgca gccacagtcc gtttgatctc cagtttggta cc                     42

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gatcgaattc ctaacactct ccgcggttga agctctttg                         39

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gatcgaattc taactttaag aaggagatat acatatg                           37

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 49
ggactgaacc agttggactt cggccatcgc tggtttgggca gc                    42

<210> SEQ ID NO 50
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
accctggtta ccgtctcctc agcctccacc aagggcccat c                     41

<210> SEQ ID NO 51
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gatgggccct tggtggaggc tgaggagacg gtaaccaggg tac                   43

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gatcgagctc tgctttcttg tccaccttgg tgttgc                           36

<210> SEQ ID NO 53
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cccaaatctt gcgctgcaga ctacaaagac gacgacgaca aatagctcga gc         52

<210> SEQ ID NO 54
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttaagctcga gctatttgtc gtcgtcgtct ttgtagtctg cagcgcaaga tttggg     56

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
```

```
gaagacgtcg ctgtttac                                              18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ggtaccaagc ttgagatc                                              18

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ctactgcgcg cgtgaaaaag                                            20

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gggtcagggg accctgg                                               17

<210> SEQ ID NO 59
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(32)
<223> OTHER INFORMATION: a, c, g, or t
<220> FEATURE:
<221> NAME/KEY: modified_base
<222> LOCATION: (34)..(35)
<223> OTHER INFORMATION: a, c, g, or t
<220> FEATURE:
<221> NAME/KEY: modified_base
<222> LOCATION: (37)..(38)
<223> OTHER INFORMATION: a, c, g, or t
<220> FEATURE:
<221> NAME/KEY: modified_base
<222> LOCATION: (40)..(41)
<223> OTHER INFORMATION: a, c, g, or t
<220> FEATURE:
<221> NAME/KEY: modified_base
<222> LOCATION: (43)..(44)
<223> OTHER INFORMATION: a, c, g, or t
<220> FEATURE:
<221> NAME/KEY: modified_base
<222> LOCATION: (46)..(47)
<223> OTHER INFORMATION: a, c, g, or t
<220> FEATURE:
<221> NAME/KEY: modified_base
<222> LOCATION: (49)..(50)
<223> OTHER INFORMATION: a, c, g, or t
```

<400> SEQUENCE: 59
gaagacgtcg ctgtttacta ctgccagcag nnsnnsnnsn nsnnsnnsnn saccttcggt         60
ggtggtacca agcttgg                                                        77

<210> SEQ ID NO 60
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, g, or t
<220> FEATURE:
<221> NAME/KEY: modified_base
<222> LOCATION: (31)..(32)
<223> OTHER INFORMATION: a, c, g, or t
<220> FEATURE:
<221> NAME/KEY: modified_base
<222> LOCATION: (34)..(35)
<223> OTHER INFORMATION: a, c, g, or t
<220> FEATURE:
<221> NAME/KEY: modified_base
<222> LOCATION: (37)..(38)
<223> OTHER INFORMATION: a, c, g, or t
<220> FEATURE:
<221> NAME/KEY: modified_base
<222> LOCATION: (40)..(41)
<223> OTHER INFORMATION: a, c, g, or t
<220> FEATURE:
<221> NAME/KEY: modified_base
<222> LOCATION: (43)..(44)
<223> OTHER INFORMATION: a, c, g, or t
<220> FEATURE:
<221> NAME/KEY: modified_base
<222> LOCATION: (46)..(47)
<223> OTHER INFORMATION: a, c, g, or t

<400> SEQUENCE: 60
ccaagcttgg taccaccacc gaaggtsnns nnsnnsnnsn nsnnsnnctg ctggcagtag         60
taaacagcga cgtcttc                                                        77

<210> SEQ ID NO 61
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(15)
<223> OTHER INFORMATION: a, c, g, or t
<220> FEATURE:
<221> NAME/KEY: modified_base
<222> LOCATION: (17)..(18)
<223> OTHER INFORMATION: a, c, g, or t
<220> FEATURE:
<221> NAME/KEY: modified_base
<222> LOCATION: (20)..(21)
<223> OTHER INFORMATION: a, c, g, or t
<220> FEATURE:
<221> NAME/KEY: modified_base
<222> LOCATION: (23)..(24)
<223> OTHER INFORMATION: a, c, g, or t
<220> FEATURE:
<221> NAME/KEY: modified_base
<222> LOCATION: (26)..(27)
<223> OTHER INFORMATION: a, c, g, or t
<220> FEATURE:
<221> NAME/KEY: modified_base

```
<222> LOCATION: (29)..(30)
<223> OTHER INFORMATION: a, c, g, or t
<220> FEATURE:
<221> NAME/KEY: modified_base
<222> LOCATION: (32)..(33)
<223> OTHER INFORMATION: a, c, g, or t
<220> FEATURE:
<221> NAME/KEY: modified_base
<222> LOCATION: (35)..(36)
<223> OTHER INFORMATION: a, c, g, or t
<220> FEATURE:
<221> NAME/KEY: modified_base
<222> LOCATION: (38)..(39)
<223> OTHER INFORMATION: a, c, g, or t
<220> FEATURE:
<221> NAME/KEY: modified_base
<222> LOCATION: (41)..(42)
<223> OTHER INFORMATION: a, c, g, or t

<400> SEQUENCE: 61
ctactgcgcg cgtnnsnnsn nsnnsnnsnn snnsnnsnns nnsttcgctt actggggtca      60
ggggacccct                                                            70

<210> SEQ ID NO 62
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(30)
<223> OTHER INFORMATION: a, c, g, or t
<220> FEATURE:
<221> NAME/KEY: modified_base
<222> LOCATION: (32)..(33)
<223> OTHER INFORMATION: a, c, g, or t
<220> FEATURE:
<221> NAME/KEY: modified_base
<222> LOCATION: (35)..(36)
<223> OTHER INFORMATION: a, c, g, or t
<220> FEATURE:
<221> NAME/KEY: modified_base
<222> LOCATION: (38)..(39)
<223> OTHER INFORMATION: a, c, g, or t
<220> FEATURE:
<221> NAME/KEY: modified_base
<222> LOCATION: (41)..(42)
<223> OTHER INFORMATION: a, c, g, or t
<220> FEATURE:
<221> NAME/KEY: modified_base
<222> LOCATION: (44)..(45)
<223> OTHER INFORMATION: a, c, g, or t
<220> FEATURE:
<221> NAME/KEY: modified_base
<222> LOCATION: (47)..(48)
<223> OTHER INFORMATION: a, c, g, or t
<220> FEATURE:
<221> NAME/KEY: modified_base
<222> LOCATION: (50)..(51)
<223> OTHER INFORMATION: a, c, g, or t
<220> FEATURE:
<221> NAME/KEY: modified_base
<222> LOCATION: (53)..(54)
<223> OTHER INFORMATION: a, c, g, or t
<220> FEATURE:
<221> NAME/KEY: modified_base
<222> LOCATION: (56)..(57)
<223> OTHER INFORMATION: a, c, g, or t

<400> SEQUENCE: 62
aggggtcccc tgacccagt aagcgaasnn snnsnnsnns nnsnnsnnsn nsnnsnnacg       60
cgcgcagtag                                                            70
```

<210> SEQ ID NO 63
<211> LENGTH: 54
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (15)
<223> OTHER INFORMATION: a, c, g, or t
<220> FEATURE:
<221> NAME/KEY: modified_base
<222> LOCATION: (18)..(19)
<223> OTHER INFORMATION: a, c, g, or t
<220> FEATURE:
<221> NAME/KEY: modified_base
<222> LOCATION: (22)
<223> OTHER INFORMATION: a, c, g, or t
<220> FEATURE:
<221> NAME/KEY: modified_base
<222> LOCATION: (25)
<223> OTHER INFORMATION: a, c, g, or t
<220> FEATURE:
<221> NAME/KEY: modified_base
<222> LOCATION: (28)
<223> OTHER INFORMATION: a, c, g, or t
<220> FEATURE:
<221> NAME/KEY: modified_base
<222> LOCATION: (38)
<223> OTHER INFORMATION: a, c, g, or t
<220> FEATURE:
<221> NAME/KEY: modified_base
<222> LOCATION: (41)
<223> OTHER INFORMATION: a, c, g, or t

<400> SEQUENCE: 63
gcgctgcagg ayggncgnna cnccnggntg tkcvaggnvc nttagctcga gcta        54

<210> SEQ ID NO 64
<211> LENGTH: 54
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (14)
<223> OTHER INFORMATION: a, c, g, or t
<220> FEATURE:
<221> NAME/KEY: modified_base
<222> LOCATION: (17)
<223> OTHER INFORMATION: a, c, g, or t
<220> FEATURE:
<221> NAME/KEY: modified_base
<222> LOCATION: (27)
<223> OTHER INFORMATION: a, c, g, or t
<220> FEATURE:
<221> NAME/KEY: modified_base
<222> LOCATION: (30)
<223> OTHER INFORMATION: a, c, g, or t
<220> FEATURE:
<221> NAME/KEY: modified_base
<222> LOCATION: (33)
<223> OTHER INFORMATION: a, c, g, or t
<220> FEATURE:
<221> NAME/KEY: modified_base
<222> LOCATION: (36)
<223> OTHER INFORMATION: a, c, g, or t

<400> SEQUENCE: 64
tagctcgagc taangbncct bgmacanccn ggngtnccgc ccgtcctgca gcgc        54

```
<210> SEQ ID NO 65
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)
<223> OTHER INFORMATION: a, c, g, or t
<220> FEATURE:
<221> NAME/KEY: modified_base
<222> LOCATION: (18)..(19)
<223> OTHER INFORMATION: a, c, g, or t
<220> FEATURE:
<221> NAME/KEY: modified_base
<222> LOCATION: (22)
<223> OTHER INFORMATION: a, c, g, or t
<220> FEATURE:
<221> NAME/KEY: modified_base
<222> LOCATION: (25)
<223> OTHER INFORMATION: a, c, g, or t
<220> FEATURE:
<221> NAME/KEY: modified_base
<222> LOCATION: (28)
<223> OTHER INFORMATION: a, c, g, or t
<220> FEATURE:
<221> NAME/KEY: modified_base
<222> LOCATION: (38)
<223> OTHER INFORMATION: a, c, g, or t
<220> FEATURE:
<221> NAME/KEY: modified_base
<222> LOCATION: (41)
<223> OTHER INFORMATION: a, c, g, or t
<220> FEATURE:
<221> NAME/KEY: modified_base
<222> LOCATION: (48)
<223> OTHER INFORMATION: a, c, g, or t
<220> FEATURE:
<221> NAME/KEY: modified_base
<222> LOCATION: (51)..(52)
<223> OTHER INFORMATION: a, c, g, or t
<220> FEATURE:
<221> NAME/KEY: modified_base
<222> LOCATION: (55)
<223> OTHER INFORMATION: a, c, g, or t
<220> FEATURE:
<221> NAME/KEY: modified_base
<222> LOCATION: (58)
<223> OTHER INFORMATION: a, c, g, or t
<220> FEATURE:
<221> NAME/KEY: modified_base
<222> LOCATION: (61)
<223> OTHER INFORMATION: a, c, g, or t
<220> FEATURE:
<221> NAME/KEY: modified_base
<222> LOCATION: (71)
<223> OTHER INFORMATION: a, c, g, or t
<220> FEATURE:
<221> NAME/KEY: modified_base
<222> LOCATION: (74)
<223> OTHER INFORMATION: a, c, g, or t

<400> SEQUENCE: 65
gcgctgcagg ayggncgnna cnccnggntg tkcvaggnvc ntgayggncg nnacnccngg      60
ntgtkcvagg nvcnttagct cgagcta                                         87

<210> SEQ ID NO 66
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (14)
<223> OTHER INFORMATION: a, c, g, or t
<220> FEATURE:
<221> NAME/KEY: modified_base
<222> LOCATION: (17)
<223> OTHER INFORMATION: a, c, g, or t
<220> FEATURE:
<221> NAME/KEY: modified_base
<222> LOCATION: (27)
<223> OTHER INFORMATION: a, c, g, or t
<220> FEATURE:
<221> NAME/KEY: modified_base
<222> LOCATION: (30)
<223> OTHER INFORMATION: a, c, g, or t
<220> FEATURE:
<221> NAME/KEY: modified_base
<222> LOCATION: (33)
<223> OTHER INFORMATION: a, c, g, or t
<220> FEATURE:
<221> NAME/KEY: modified_base
<222> LOCATION: (36)
<223> OTHER INFORMATION: a, c, g, or t
<220> FEATURE:
<221> NAME/KEY: modified_base
<222> LOCATION: (47)
<223> OTHER INFORMATION: a, c, g, or t
<220> FEATURE:
<221> NAME/KEY: modified_base
<222> LOCATION: (50)
<223> OTHER INFORMATION: a, c, g, or t
<220> FEATURE:
<221> NAME/KEY: modified_base
<222> LOCATION: (60)
<223> OTHER INFORMATION: a, c, g, or t
<220> FEATURE:
<221> NAME/KEY: modified_base
<222> LOCATION: (63)
<223> OTHER INFORMATION: a, c, g, or t
<220> FEATURE:
<221> NAME/KEY: modified_base
<222> LOCATION: (66)
<223> OTHER INFORMATION: a, c, g, or t
<220> FEATURE:
<221> NAME/KEY: modified_base
<222> LOCATION: (69)
<223> OTHER INFORMATION: a, c, g, or t

<400> SEQUENCE: 66
tagctcgagc taangbncct bgmacanccn ggngtnccgc ccgtcangbn cctbgmacan      60
ccnggngtnc cgcccgtcct gcagcgc                                         87
```